(12) United States Patent
Honda et al.

(10) Patent No.: US 11,977,214 B2
(45) Date of Patent: May 7, 2024

(54) PHASE DIFFERENCE OBSERVATION APPARATUS AND CELL TREATMENT APPARATUS

(71) Applicant: KATAOKA CORPORATION, Kyoto (JP)

(72) Inventors: Shoichi Honda, Kyoto (JP); Junichi Matsumoto, Kyoto (JP); Tadao Morishita, Kyoto (JP)

(73) Assignee: Kataoka Corporation, Kyoto (JP)

( * ) Notice: Subject to any disclaimer, the term of this patent is extended or adjusted under 35 U.S.C. 154(b) by 583 days.

(21) Appl. No.: 16/648,950

(22) PCT Filed: Aug. 17, 2018

(86) PCT No.: PCT/JP2018/030464
§ 371 (c)(1),
(2) Date: Mar. 19, 2020

(87) PCT Pub. No.: WO2019/064984
PCT Pub. Date: Apr. 4, 2019

(65) Prior Publication Data
US 2020/0271913 A1    Aug. 27, 2020

(30) Foreign Application Priority Data

Sep. 28, 2017   (JP) .................. 2017-189170
Jun. 8, 2018    (JP) .................. 2018-110020

(51) Int. Cl.
*G02B 21/06*       (2006.01)
*G02B 21/00*       (2006.01)
(Continued)

(52) U.S. Cl.
CPC ............. *G02B 21/14* (2013.01); *G02B 21/06* (2013.01); *G02B 21/26* (2013.01); *G02B 27/52* (2013.01)

(58) Field of Classification Search
CPC ............... G02B 21/00; G02B 21/0004; G02B 21/0032; G02B 21/0052; G02B 21/0056;
(Continued)

(56) References Cited

U.S. PATENT DOCUMENTS 6,238,911 B1   5/2001  Kasahara
7,382,532 B2 *  6/2008  Okugawa ........... G02B 21/0088
                                                 359/395
(Continued)

FOREIGN PATENT DOCUMENTS

JP   2000-004871    1/2000
JP   2005-004088    1/2005
(Continued)

OTHER PUBLICATIONS

International Search Report issued in International Application No. PCT/JP2018/030464, dated Nov. 13, 2018, 4 pages.
(Continued)

*Primary Examiner* — Thong Q Nguyen
(74) *Attorney, Agent, or Firm* — HSML P.C.

(57) ABSTRACT

A phase difference observation apparatus includes a light source; an illumination guide to guide illumination light from the light source to an observation target object in a cell culture vessel; an optical imager to form an optical image of the observation target object on an image sensor; and a controller. The illumination guide includes a spatial modulator to change an intensity distribution of the illumination light; the controller contains intensity distribution correction information associating a position of the imaging guide with respect to the cell culture vessel with an intensity distribution of illumination light at the position of the optical imager; the controller acquires imaging system position information, which is the position of the optical imager; and the controller changes an intensity distribution of illumina-
(Continued)

tion light in the spatial modulator on the basis of the imaging system position information and the intensity distribution correction information.

17 Claims, 19 Drawing Sheets

(51) Int. Cl.
   *G02B 21/14* (2006.01)
   *G02B 21/26* (2006.01)
   *G02B 27/52* (2006.01)

(58) Field of Classification Search
   CPC ............... G02B 21/006; G02B 21/008; G02B 21/0088; G02B 21/06; G02B 21/086; G02B 21/14; G02B 21/26; G02B 27/00; G02B 27/0025; G02B 27/0068; G02B 27/52; G02B 27/62
   USPC .................................................. 359/368–398
   See application file for complete search history.

(56) References Cited

U.S. PATENT DOCUMENTS

| | | | | |
|---|---|---|---|---|
| 7,709,773 | B2* | 5/2010 | Yamashita | G01N 21/6456 |
| | | | | 250/201.3 |
| 9,261,690 | B2* | 2/2016 | Fukutake | G02B 21/367 |
| 9,575,303 | B2* | 2/2017 | Takamizawa | G02B 21/06 |
| 2004/0051051 | A1* | 3/2004 | Kato | G01N 21/6428 |
| | | | | 250/458.1 |
| 2009/0161209 | A1 | 6/2009 | Hayashi et al. | |
| 2012/0099172 | A1 | 4/2012 | Ohki | |
| 2012/0257040 | A1 | 10/2012 | Koebler et al. | |
| 2013/0120833 | A1* | 5/2013 | Hirano | G02B 21/24 |
| | | | | 359/385 |
| 2015/0049376 | A1* | 2/2015 | Matsumoto | G02B 26/06 |
| | | | | 359/238 |
| 2015/0309296 | A1 | 10/2015 | Dowaki et al. | |
| 2015/0355446 | A1 | 12/2015 | Kues et al. | |
| 2018/0113294 | A1 | 4/2018 | Shiraishi | |

FOREIGN PATENT DOCUMENTS

| | | | |
|---|---|---|---|
| JP | 2008-181070 | | 8/2008 |
| JP | 2009-156977 | | 7/2009 |
| JP | 2010-039262 | | 2/2010 |
| JP | 2010-271537 | | 12/2010 |
| JP | 2011-002698 | | 1/2011 |
| JP | 2012-013888 | | 1/2012 |
| JP | 2012-088530 | | 5/2012 |
| JP | 2016-071117 | | 5/2016 |
| JP | 2017-015857 | | 1/2017 |
| JP | 2019-45737 | * | 3/2019 |
| WO | 2013/114430 | | 8/2013 |
| WO | 2014/091661 | | 6/2014 |

OTHER PUBLICATIONS

Office Action issued in corresponding Chinese Patent Application No. 201880061704.6, dated May 27, 2021, 13 pages w/translation.

* cited by examiner

FIG. 19

| Dish observation image before and after correction | | | | |
|---|---|---|---|---|
| Observation position | a | b | c | d |
| Before correction | | | | |
| After correction | | | Corrected image 2 / Corrected image 1 / Corrected image 3 | Corrected image 4 / Corrected image 5 / Corrected image 6 |
| After integration | | | | |

PHASE DIFFERENCE OBSERVATION APPARATUS AND CELL TREATMENT APPARATUS

TECHNICAL FIELD

The present invention relates to a phase difference observation apparatus and a cell treatment apparatus.

BACKGROUND ART

When observing the vicinity of the wall surface of a cell culture vessel, there is a case that, due to the curve of the liquid surface of the culture solution by the surface tension (i.e., due to meniscus), light is refracted to be reflected in a phase difference image. In addition, when the light is reflected in the phase difference image, a problem has arisen that the background of the phase difference image is dark, which causes loss of the phase difference effect in which an observation target object in a cell culture vessel appears bright (deterioration of the phase difference image).

As a method for preventing the deterioration of the phase difference image, there has been proposed an apparatus for handling the deterioration of the phase difference image by moving a ring slit (aperture ring) and a condenser lens of a phase difference observation apparatus (Patent Literature 1).

However, in the apparatus of Patent Literature 1 (WO 2014/091661), in order to sequentially adjust the positions of the ring slit and the condenser lens, an imaging unit that can take the images of an aperture ring and a phase plate is provided separately from the imaging unit for observation, and the movement amounts of the ring slit and the condenser lens are calculated on the basis of the obtained images of the aperture ring and the phase plate. Then, the positions of the ring slit and the condenser lens are adjusted on the basis of the obtained movement amounts. Thus, there is a problem that an additional configuration is required for adjusting the positions of the ring slit and the condenser lens which increases the size of the phase difference observation apparatus.

SUMMARY OF THE INVENTION

Technical Problem

It is an object of the present invention to provide a phase difference observation apparatus that can reduce the size of the apparatus by not requiring an additional imaging unit and can suppress deterioration of the phase difference image due to the meniscus, for example.

Solution to Problem

In order to achieve the above object, the present invention provides a phase difference observation apparatus, including: a light source; an illumination optical system that guides illumination light from the light source to an observation target object in a cell culture vessel; an imaging optical system that forms an optical image of the observation target object on an image sensor; and a control unit, wherein the illumination optical system includes a spatial modulator that changes an intensity distribution of the illumination light, the control unit contains intensity distribution correction information associating a position of the imaging optical system with respect to the cell culture vessel with an intensity distribution of illumination light at the position of the imaging optical system, the control unit acquires imaging system position information, which is the position of the imaging optical system, and the control unit changes an intensity distribution of illumination light in the spatial modulator on the basis of the imaging system position information and the intensity distribution correction information.

The present invention also provides a cell treatment apparatus including: an observation unit that can observe an observation target object in a cell culture vessel; a laser irradiation unit that can irradiate the observation target object with lasers; and a control unit that controls at least one of the observation unit or the laser irradiation unit, wherein the observation unit is the phase difference observation apparatus according to the present invention.

Advantageous Effects of Invention

According to the phase difference observation apparatus of the present invention, for example, since an additional imaging unit is not required, the size of the apparatus can be reduced, and deterioration of the phase difference image due to the meniscus can be suppressed.

BRIEF DESCRIPTION OF DRAWINGS

FIG. 19 is a photograph showing a phase difference image taken by the phase difference observation apparatus of the present invention in Example 1.

DESCRIPTION OF EMBODIMENTS

Figure 1:
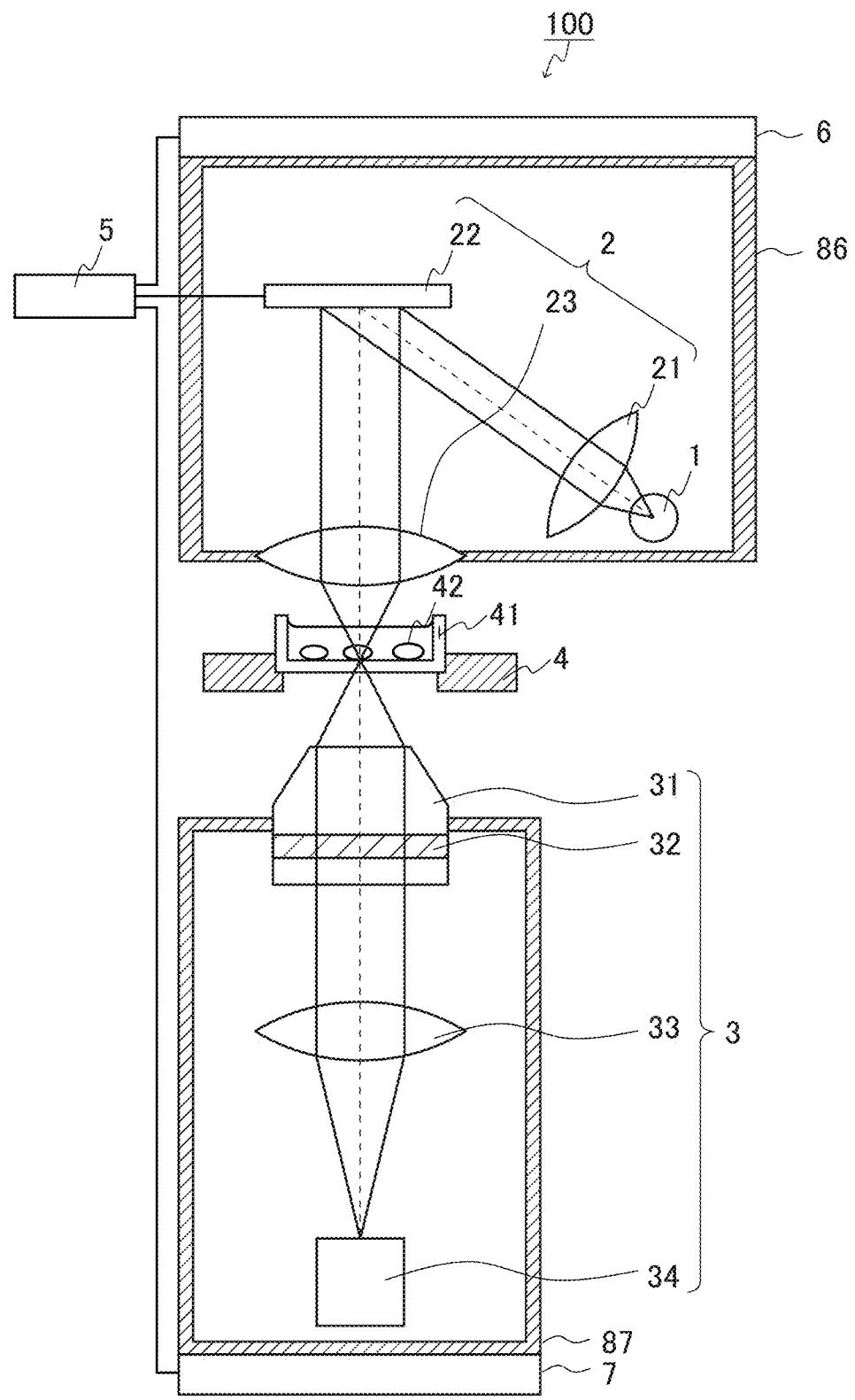
FIG. 1 is a schematic view showing an example of the phase difference observation apparatus according to the first embodiment.

Hereinafter, in the present invention, the "Z-axis direction" refers to a direction perpendicular to the plane direction of the phase plate, the "X-axis direction" refers to one direction in the plane (XY plane) direction of the phase plate, and the "Y-axis direction" refers to a direction orthogonal to the X-axis direction in the plane direction of the phase plate.

In the present invention, "deterioration of the phase difference image" means, for example, that the phase difference effect in the phase difference image is reduced, i.e, the contrast is lowered.

The phase difference observation apparatus and the cell treatment apparatus of the present invention are described in detail below with reference to the drawings. The present invention, however, is not limited by the following description. Note that there may be cases where the same reference signs are given to the same components in FIGS. 1 to 19 below and descriptions thereof are omitted. Furthermore, for convenience in explanation, the structure of each component shown in the drawings may be appropriately simplified, and the size, the ratio, and the like of components may be schematically shown and different from actual ones. Regarding the descriptions of the embodiments, reference can be made to each other unless otherwise stated.

First Embodiment

The present embodiment relates to an example of a phase difference observation apparatus. FIG. 1 is a schematic cross-sectional view showing the configuration of a phase difference observation apparatus 100 according to the first embodiment. As shown in FIG. 1, the phase difference observation apparatus 100 includes a light source 1, an illumination optical system 2, an imaging optical system 3, a stage 4, a control unit 5, a first moving unit 6, and a second moving unit 7 as main components. The illumination optical system 2 includes a light source lens 21, a digital micromirror device (DMD) 22, and a condenser lens 23, which are placed in this order along the optical path of the illumination light emitted from the light source 1. The DMD 22, which is the spatial modulator, is placed as a component having a function equivalent to a ring slit in a common phase difference observation apparatus. The light source 1, and the light source lens 21 and the DMD 22 of the illumination optical system 2 are accommodated in a housing 86 having an opening. The condenser lens 23 of the illumination optical system 2 is placed at an opening of the housing 86 such that the illumination light (reflected light) guided from the DMD 22 can be guided to the observation target object 42 in the cell culture vessel 41. The imaging optical system 3 includes an objective lens 31 provided with a phase plate 32, an imaging lens 33, and an image sensor 34, which are placed in this order along the optical path of the illumination light. The imaging lens 33 and the image sensor 34 of the imaging optical system 3 are accommodated in a housing 87. The objective lens 31 is placed at an opening of the housing 87 such that an optical image of the observation target object 42 can be formed on the image sensor 34. The cell culture vessel 41 containing the observation target object 42 is placed on a stage 4. The stage 4 is placed between the illumination optical system 2 and the imaging optical system 3 in the optical path of the illumination light. The control unit 5 is electrically connected to the DMD 22, the first moving unit 6, and the second moving unit 7. The first moving unit 6 is placed so as to be in contact with the housing 86 and so as to be able to move the light source 1 and the illumination optical system 2. The second moving unit 7 is placed so as to be in contact with the housing 87 and so as to be able to move the imaging optical system 3. While the phase difference observation apparatus 100 of the present embodiment includes the stage 4, the cell culture vessel 41, the first moving unit 6, the second moving unit 7, the housing 86, and the housing 87, these components are optional, and the phase difference observation apparatus 100 may or may not include them.

The light source 1 is, for example, a light source that generates illumination light to be emitted to the observation target object 42 that is cultured in the cell culture vessel 41. The light source 1 is not particularly limited, and, for example, a known light source can be used. Specific examples thereof include a halogen lamp, a tungsten lamp, a white light emitting diode (LED), a monochromatic LED, and a semiconductor laser.

The illumination optical system 2 is, for example, an optical system that guides the illumination light from the light source 1 to the observation target object 42 in the cell culture vessel 41. While the illumination optical system 2 includes the light source lens 21, the DMD 22, and the condenser lens 23 in the phase difference observation apparatus 100 of the present embodiment, the light source lens 21 and the condenser lens 23 are optional, and the phase difference observation apparatus 100 may or may not include them. The illumination optical system 2 may include, for example, a lens such as a field diaphragm, an aperture diaphragm, a relay lens, a collimate lens, a fly-eye lens, a diffusion plate, or the like; a prism such as an internal totally reflective prism (TIR prism), or the like; and a mirror.

The light source lens 21 is, for example, a lens that collects the illumination light emitted from the light source 1. As the light source lens 21, for example, a known lens or a known lens system can be used, and a lens or a lens system to serve as a Kohler illumination that can uniformly illuminate the surface on which the observation target object 42 is present is preferable.

The DMD 22 changes, for example, the intensity distribution of illumination light emitted from the light source 1. Specifically, for example, the DMD 22 guides the illumination light emitted from the light source 1 by reflecting it toward the observation target object 42. As described above, the DMD 22 has a function equivalent to a ring slit in a common phase difference observation apparatus. Thus, the DMD 22 freely changes the intensity distribution of illumination light by shaping the position, shape, and size of the illumination light so as to obtain the phase difference effect in the phase difference image (image data) taken by the image sensor 34 by combining with the phase plate 32, for example. The position, shape, and size of the illumination light are controlled by the control unit 5, for example, as described below. As a specific example, when the liquid level of the culture solution in the cell culture vessel 41 is horizontal, the shape of the illumination light is, for example, a ring shape. The shape of the illumination light means, for example, the shape of the illumination light in a plane perpendicular to the optical axis direction between the DMD 22 and the objective lens 31. The DMD 22 is not particularly limited, and known DMD elements can be used. The DMD 22 includes, for example, a plurality of reflective surfaces that are rotatable about mutually-parallel rotation axes. In this case, for example, by changing the angles of the plurality of reflection surfaces respectively, the position, shape, and size of the illumination light are shaped.

The position of the DMD 22 in the phase difference observation apparatus 100 is not particularly limited. For example, since a larger contrast (phase difference effect) can be obtained in the phase difference image of the observation target object 42, it is preferable to dispose the DMD 22 at a position optically conjugate to the pupil (pupil position) of the imaging optical system 3, more specifically, at a position optically conjugate to the phase plate 32.

While the phase difference observation apparatus 100 of the present embodiment includes the DMD 22 as the spatial modulator, any component that can change the intensity distribution of illumination light can be used as the spatial modulator. Specific examples of the spatial modulator include a liquid crystal panel, an array in which electrochromic elements are placed in an array, and an array in which light emitting elements such as organic electroluminescence (EL) elements are placed in an array. When the spatial modulator is the liquid crystal panel or the electrochromic element, the light source 1, the illumination optical system 2, the stage 4, and the imaging optical system 3 are placed in this order on a straight line, for example. When the spatial modulator is the light emitting element, the spatial modulator may also serve as the light source 1, for example. The spatial modulator freely changes the intensity distribution of illumination light by shaping the position, shape, and size of the illumination light so as to obtain the phase difference effect in the image taken by the image sensor 34 by combining with the phase plate 32 in the same manner as the DMD 22, for example. The position of the spatial modulator is not particularly limited, and is, for example, the same as the position of the DMD 22.

The condenser lens 23 is, for example, a lens that focuses the illumination light on the observation target object 42. As the condenser lens 23, for example, a known lens or lens system can be used.

The imaging optical system 3 is, for example, an optical system that forms an optical image of the observation target object 42 on the image sensor 34. While the imaging optical system 3 includes the objective lens 31 provided with the phase plate 32, the imaging lens 33, and the image sensor 34 in the phase difference observation apparatus 100 of the present embodiment, the objective lens 31 provided with the phase plate 32 and the imaging lens 33 are optional, and the phase difference observation apparatus 100 may or may not include them. The imaging optical system 3 may include other components such as a mirror and the like, for example.

The objective lens 31 is, for example, a lens that magnifies an image of the observation target object 42 to an intended magnification. The objective lens 31 can be, for example, a known lens or a known lens system, and can be appropriately selected depending on an intended magnification. While the phase difference observation apparatus 100 of the present embodiment includes one objective lens 31, the phase difference observation apparatus 100 may include two or more objective lenses 31. When the phase difference observation apparatus 100 includes two or more objective lenses 31, it is preferable that each of the objective lenses 31 can magnify the image to different magnifications. While the objective lens 31 is provided with the phase plate 32, as described above, the phase plate 32 is optional, and the objective lens 31 may or may not be provided with the phase plate 32.

The phase plate 32, for example, manipulates the phase of a part of the incident light. While the objective lens 31 is provided with the phase plate 32, i.e., the objective lens 31 and the phase plate 32 are integrally formed in the phase difference observation apparatus 100 of the present embodiment, the phase plate 32 may be formed independently of the objective lens 31. The phase plate 32 may be configured by forming a wavelength plate such as a ¼ wavelength plate and an optical absorbent filter such as a neutral density filter in a ring form, for example.

The imaging lens 33 is, for example, a lens that forms an optical image of the observation target object 42 on the image sensor 34. As the imaging lens 33, for example, a known lens or a known lens system can be used.

The image sensor 34 is, for example, a device that takes an optical image (phase difference image) of the observation target object 42. As the image sensor 34, for example, a known image sensor can be used, and specific examples thereof include devices provided with a charge-coupled device (CCD), a complementary metal oxide semiconductor (CMOS), and the like. The imaging surface of the image sensor 34 is preferably placed at a position optically conjugate to the observation target object 42, for example, so that a clearer phase difference image of the observation target object 42 can be obtained. The image sensor 34 may output the taken phase difference image of the observation target object 42 to the display device via the control unit 5, for example. In this case, the image sensor 34 is electrically connected to the control unit 5.

The stage 4 supports, for example, the cell culture vessel 41. The stage 4 has, for example, a recess in which the cell culture vessel 41 can be placed, and has an opening at a position corresponding to the cell culture vessel 41.

While the position of the stage 4 is fixed in the phase difference observation apparatus 100, i.e., the stage 4 does not move, the stage 4 may be movable. When the stage 4 is movable, the stage 4 is moved by, for example, a known moving unit (drive unit). The moving direction of the stage 4 is not particularly limited, and is, for example, any one direction, two directions, or all directions of the X-axis direction, the Y-axis direction, and the Z-axis direction. In the phase difference observation apparatus 100 of the present embodiment, the position of the stage 4 is fixed. Therefore, the phase difference observation apparatus 100 of the present embodiment can prevent the liquid surface of the culture solution in the cell culture vessel 41 from fluctuating when the stage 4 moves in the phase difference observation apparatus in which the stage 4 is movable, for example. In addition, the phase difference observation apparatus 100 of the present embodiment is suitable for automatic imaging of the cell culture vessel 41 because, for example, disturbance of the phase difference image of the observation target object 42 due to fluctuation of the liquid surface of the culture solution can be suppressed. Furthermore, according to the phase difference observation apparatus 100 of the present embodiment, since the waiting time until the fluctuation of the liquid surface of the culture liquid subsides can be reduced, for example, the whole surface of the cell culture vessel 41 can be imaged in a shorter time.

While the phase difference observation apparatus 100 of the present embodiment includes the stage 4 as the cell culture vessel placement unit, any component, in which the cell culture vessel 41 can be placed and the observation target object 42 in the cell culture vessel 41 can be observed, can be used as the cell culture vessel placement unit. While the stage 4 has an opening in the present embodiment, a light transmissive material may be placed on the imaging optical system 3 side of the opening, for example. Examples of the light transmissive material include a transparent glass plate and an acrylic plate. The position of the cell culture vessel placement unit may be fixed in the phase difference observation apparatus or the cell culture vessel placement unit may be movable in the phase difference observation apparatus, for example. Regarding the movement of the cell culture vessel placement unit, reference can be made to the above description as to the movement of the stage 4, for example.

The cell culture vessel placement unit (stage 4) may further include, for example, a temperature regulating unit for regulating the temperature of the cell culture vessel 41. By providing the temperature regulating unit, the culture condition during the treatment of the cells in the cell culture vessel 41 can be kept constant, and damage to the observation target object 42 can be reduced at the time of imaging the observation target object 42 and at the time of cell treatment to be described below, for example. The temperature regulating unit may be, for example, a heating unit such as a heater.

The cell culture vessel placement unit (stage 4) may further include a pH regulating unit for regulating the pH of the culture solution in the cell culture vessel 41, for example. By providing the pH regulating unit, the culture condition during the treatment of the cells in the cell culture vessel can be kept constant, and damage to the cells during cell treatment can be reduced, for example. As the pH regulating unit, for example, a carbon dioxide concentration regulating unit or the like can be used, and as a specific example, a connecting portion connected to a carbon dioxide supply unit outside the phase difference observation apparatus 100 can be used.

The cell culture vessel 41 is not particularly limited, and may be, for example, a culture vessel such as a known dish, a known flask, or the like used for cell culture. The material for forming the cell culture vessel 41 is not particularly limited, and may be, for example, a material that transmits the laser emitted by the laser irradiation unit to be described below, and specific examples thereof include plastics and glasses that transmit lasers. Examples of the plastic include polystyrene polymers, acrylic polymers (polymethyl methacrylate (PMMA) and the like), polyvinylpyridine polymers (poly(4-vinylpyridine), 4-vinylpyridine-styrene copolymers and the like), silicone polymers (polydimethylsiloxane and the like), polyolefin polymers (polyethylene, polypropylene, polymethylpentene and the like), polyester polymers (polyethylene terephthalate (PET), polyethylene naphthalate (PEN), and the like), polycarbonate polymers, and epoxy polymers.

In a case where the observation target object 42 in the cell culture vessel 41 is subjected to laser treatment, the cell culture vessel 41 preferably includes, for example, a polymer including a dye structure (chromophore) that absorbs the laser, or a laser absorbing layer formed of a photoacid generator that absorbs the laser and generates an acidic material, on the bottom surface of the inside (observation target object 42 side) of the cell culture vessel 41. As to the dye structure and the photoacid generator, reference can be made to, for example, the description of Japanese Patent No. 6033980. By providing the laser absorbing layer in the cell culture vessel 41, the energy of the laser can be converted into heat, acid, or the like when the laser irradiation unit of the cell treatment apparatus to be described below emits the laser, for example, thereby killing, liberating, or the like the cells present above the laser absorbing layer.

The observation target object 42 is not particularly limited, and may be a cell, a cell mass (spheroid) composed of cells, a tissue, an organ, or the like. The cell may be, for example, a cultured cell or a cell isolated from a living body. The cell mass, the tissue, or the organ may be, for example, a cell mass, a tissue, or an organ produced from the cells, or may be a cell mass, a tissue, or an organ isolated from a living body.

Figure 2:
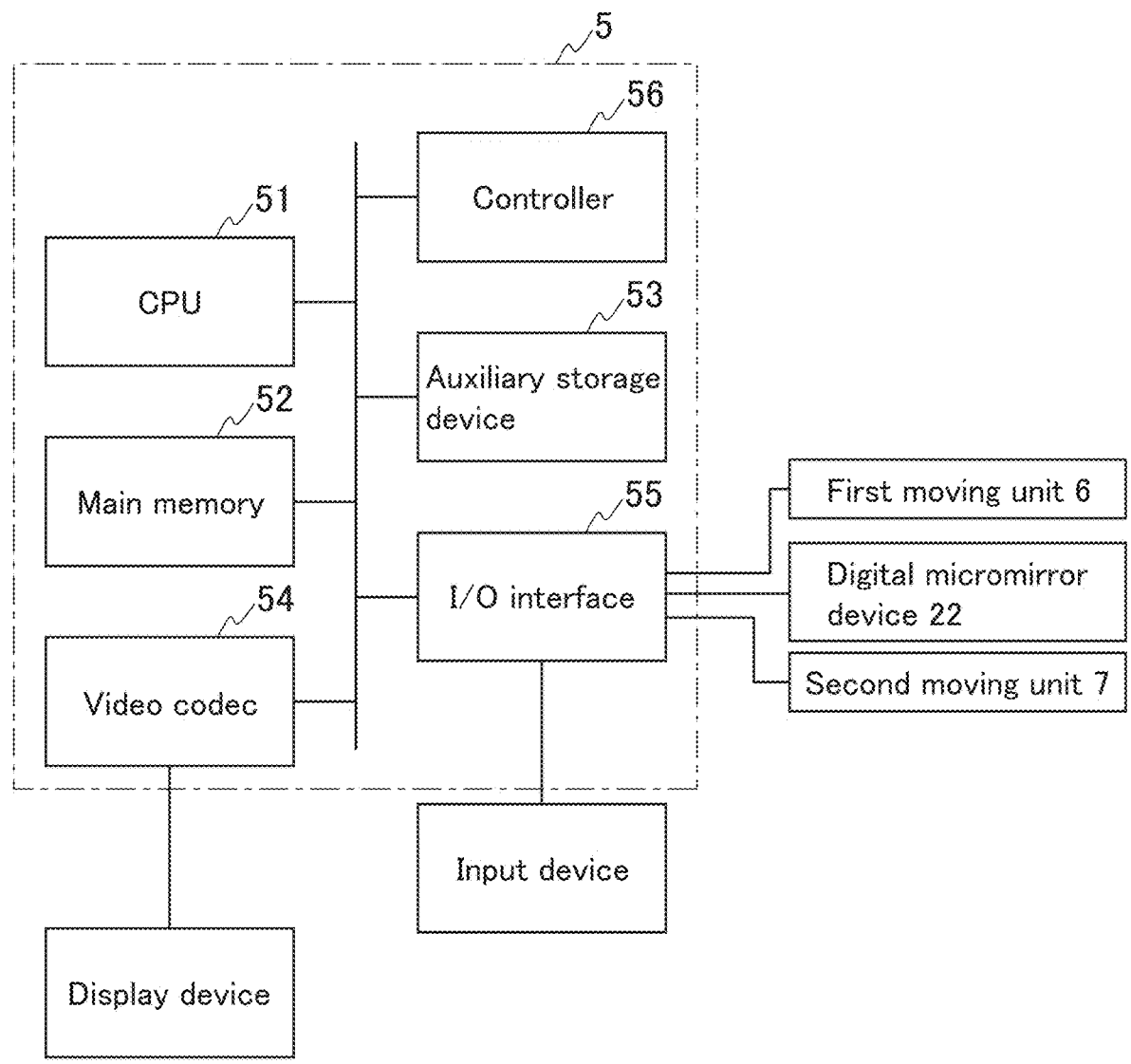
FIG. 2 is a block diagram showing an example of the control unit in the phase difference observation apparatus according to the first embodiment.

The control unit 5 has a configuration similar to a personal computer, a server computer, a workstation, or the like. FIG. 2 is a block diagram showing an example of the control unit 5 in the phase difference observation apparatus 100 according to the present embodiment. As shown in FIG. 2, the control unit 5 includes a central processing unit (CPU) 51, a main memory 52, an auxiliary storage device 53, a video codec 54, an input-output (I/O) interface 55, and the like, which are controlled by a controller (a system controller, an I/O controller, or the like) 56 and operate in cooperation with each other. The auxiliary storage device 53 can be a storage device such as a flash memory, a hard disk drive, or the like. The video codec 54 includes: a graphics processing unit (GPU) that generates a screen to be displayed based on a drawing instruction received from the CPU 51 and transmits the screen signal to a display device or the like outside the phase difference observation apparatus 100; and a video memory that temporarily stores the screen and image data, for example. The I/O interface 55 is a device that can communicate with and control the members such as the DMD 22, the first moving unit 6, the second moving unit 7, and the like. The I/O interface 55 may include a servo driver (servo controller). The I/O interface 55 may be connected to an input device outside the phase difference observation apparatus 100, for example. The display device may be, for example, monitors (for example, various image display devices such as a liquid crystal display (LCD) and a cathode ray tube (CRT) display) which output images. Examples of the input device include a touch panel, a track pad, a pointing device such as a mouse, a keyboard, and a push button which can be operated by a finger of a user.

The programs executed by the control unit 5 and the respective pieces of information are stored in the auxiliary storage device 53. The program is read into the main memory 52 and is decoded by the CPU 51 at the time of executing the program. The control unit 5 controls each member according to the program. The control of each member by the control unit 5 will be described below.

In the phase difference observation apparatus 100 according to the present embodiment, the control unit 5 has the functions of controlling the DMD 22, the first moving unit 6, and the second moving unit 7, so that a control unit does not have to be individually provided in each member, whereby the size of the device can be reduced. The present invention, however, is not limited thereto. In the phase difference observation apparatus of the present embodiment, for example, a control unit as the control unit 5 may be provided in each of the DMD 22, the first moving unit 6, and the second moving unit 7, and each member may be controlled by the control unit of each member. The phase difference observation apparatus according to the present invention may include, for example, the control unit 5 and the control units of the respective members to control the members in cooperation. The control unit 5 may be configured by one semiconductor element, may be a chip in which a plurality of semiconductor elements are packaged, or may be a substrate on which a plurality of semiconductor elements are provided.

The first moving unit 6 is, for example, a moving unit that can move the light source 1 and the illumination optical system 2. The first moving unit 6 may be, for example, a known moving unit (drive unit). The moving direction of the first moving unit 6 is not particularly limited, and is, for example, any one direction, two directions, or all directions of the X-axis direction, the Y-axis direction, and the Z-axis direction. The first moving unit 6 is preferably movable in the Z-axis direction so that the light source 1 and the illumination optical system 2 can be moved so as to position the DMD 22 and the pupil (pupil position) of the imaging optical system 3 optically conjugate to each other, and a larger contrast (phase difference effect) can be obtained in the phase difference image of the observation target object 42, for example. While the first moving unit 6 can move the light source 1 and the illumination optical system 2 in the phase difference observation apparatus 100 of the present embodiment, the first moving unit 6 may be configured to move only one of the light source 1 and the illumination optical system 2, for example. The first moving unit 6 is only required to move the light source 1 and the illumination optical system 2, for example, and can be appropriately placed depending on the moving unit to be used. The movement by the first moving unit 6 is controlled by the control unit 5, for example, as will be described below.

The second moving unit 7 is, for example, a moving unit that can move the imaging optical system 3. The second moving unit 7 may be a known moving unit (drive unit). The moving direction of the second moving unit 7 is not particularly limited, and is, for example, any one direction, two directions, or all directions of the X-axis direction, the Y-axis direction, and the Z-axis direction. The second moving unit 7 is preferably movable in the Z-axis direction so that the imaging optical system 3 can be moved so as to position the imaging surface of the image sensor 34 and the observation target object 42 optically conjugate to each other, and a clearer phase difference image of the observation target object 42 can be obtained, for example. The second moving unit 7 is only required to move the imaging optical system 3, for example, and can be appropriately placed depending on the moving unit to be used. The movement by the second moving unit 7 is controlled by the control unit 5, for example, as will be described below.

Next, the operation of the control unit 5 in the phase difference observation apparatus 100 of the present embodiment and the imaging method of the phase difference image using the phase difference observation apparatus 100 are described below.

The control unit 5 of the present embodiment contains intensity distribution correction information associating the position of the imaging optical system 3 with respect to the cell culture vessel 41 with the intensity distribution of illumination light at the position of the imaging optical system 3. Therefore, first, the intensity distribution correction information is acquired and stored in the auxiliary storage device 53 of the control unit 5. The intensity distribution correction information may be, for example, information acquired in advance by another phase difference observation apparatus or the like, information input by the user of the phase difference observation apparatus 100 of the present embodiment, or information acquired by the phase difference observation apparatus 100 of the present embodiment, and the information acquired by the phase difference observation apparatus 100 of the present embodiment is preferable because degradation of a phase difference image due to the meniscus can be suppressed more effectively. When the intensity distribution correction information is acquired using the phase difference observation apparatus 100 of the present embodiment, the intensity distribution correction information is acquired as follows.

Figure 3:
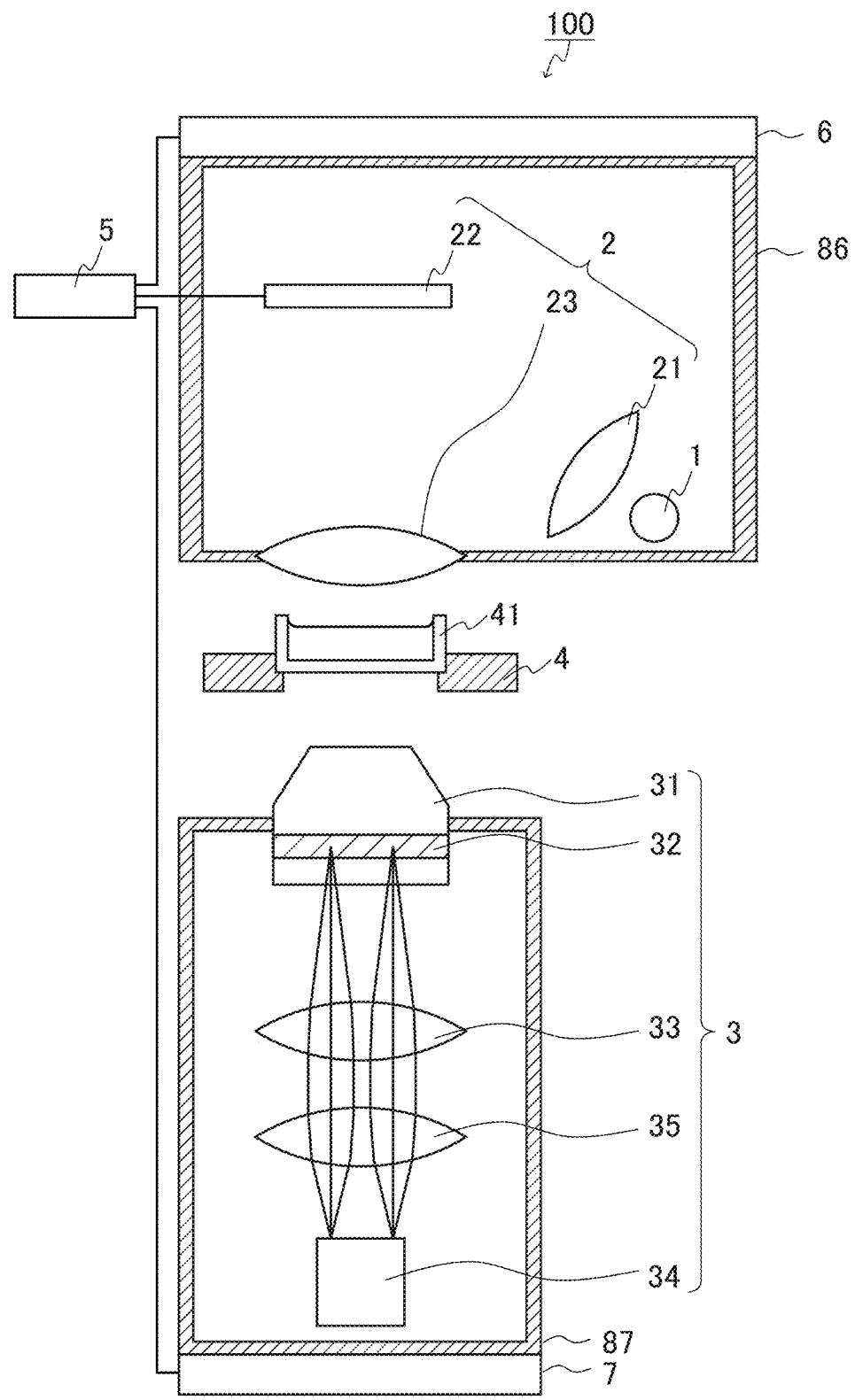
FIG. 3 is a schematic view showing an example of the phase difference observation apparatus in a case of acquiring intensity distribution correction information in the first embodiment.

FIG. 3 is a schematic view showing the configuration of the phase difference observation apparatus 100 in the case of acquiring the intensity distribution correction information. In FIG. 3, the optical path of the illumination light is not shown. As shown in FIG. 3, a cell culture vessel 41 (cell culture vessel 41 for correction) containing no observation target object 42 is placed on the stage 4 of the phase difference observation apparatus 100. At this time, the amount and type of the culture solution in the cell culture vessel 41 for correction are the same as those of the culture solution in the cell culture vessel 41 containing the observation target object 42. A phase plate imaging lens 35 is inserted between the imaging lens 33 and the image sensor 34 of the imaging optical system 3 of the phase difference observation apparatus 100. As a result, the image of the phase plate 32 and the image of the illumination light (the image of the reflected light of the DMD 22) are formed on the image sensor 34 as shown in FIG. 3. Although it is not shown, the control unit 5 is electrically connected to the image sensor 34. As the phase plate imaging lens 35, for example, a known lens or a known lens system can be used.

Next, using the phase difference observation apparatus 100 shown in FIG. 3, the cell culture vessel 41 for correction is divided into a plurality of sections, and each section is imaged (tile imaging), whereby the image of the phase plate 32 and the image of the illumination light for correction are acquired by the image sensor 34. In each imaging, the control unit 5 acquires the position of the imaging optical system 3 as imaging system position information. The imaging system position information (the position of the imaging optical system 3) includes, for example, coordinates (three-dimensional coordinates) in the XYZ axes or coordinates (two-dimensional coordinates) in the XY axes.

Figure 4A:
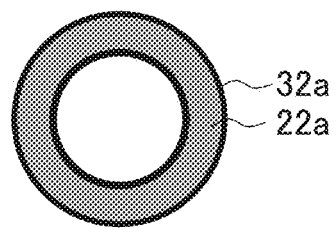
FIG. 4 is a schematic view showing an example of the image of phase plate 32 for correction and the image of illumination light taken by an image sensor in the first embodiment.
Figure 4B:
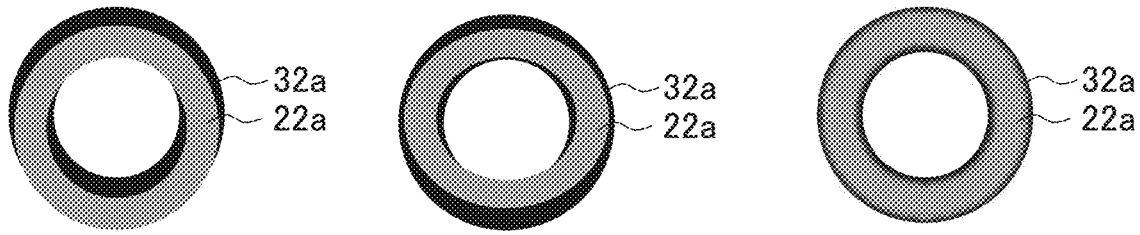

FIG. 4 is a schematic view of the image of the phase plate 32 and the image of the illumination light for correction taken by the image sensor 34. The illumination optical system 2 and the imaging optical system 3 are placed in the Z-axis direction of the horizontal plane of the culture solution in the cell culture vessel 41 for correction. At this time, when the DMD 22 and the phase plate 32 are optically conjugated and imaged by the image sensor 34, the illumination light image 22a is included in the image (phase plate image) 32a of the phase plate 32 in the imaged phase difference image (image for correction), as shown in FIG. 4A. However, as described above, when the vicinity of the wall surface of the cell culture vessel 41 is observed, the liquid surface of the culture solution forms a meniscus, which causes a lens effect. Therefore, the illumination light passing through the meniscuses is refracted, and the optical conjugate relationship between the DMD 22 and the phase plate 32 is lost. At this time, as shown in FIG. 4B, the problems that the illumination light image 22a is not included in the phase plate image 32a, deformed, and/or blurred in the image for correction arise, whereby the phase difference effect is reduced. Hence, when the problems shown in FIG. 4B arise, the control unit 5 acquires information for correcting the relationship between the illumination light image 22a and the phase plate image 32a to be the state shown in FIG. 4A as intensity distribution correction information. More specifically, the control unit 5 obtains, as to the cell culture vessel 41 for correction, the intensity distribution of illumination light with which the illumination light image 22a is included in the phase plate image 32a at each imaging position, i.e., at each position of the imaging optical system 3, in the tile imaging. That is, the control unit 5 obtains the position information of the mirror in the DMD 22 that reflects the illumination light toward the observation target object 42 when the intensity distribution of illumination light is corrected to be in the state where the illumination light image 22a is included in the phase plate image 32a, and the position information of the mirror in the DMD 22 that does not reflect the illumination light toward the observation target object 42.

The control unit 5 detects whether the illumination light image 22a is included in the phase plate image 32a in the image for correction at the time of the tile imaging. When the illumination light image 22a is not included in the phase plate image 32a, i.e., when there is a deviation between the illumination light image 22a and the image 32a of the phase plate 32, the control unit 5 obtains the position and size of the reflected light of the DMD 22 with which the illumination light image 22a is included in the phase plate image 32a. Specifically, the control unit 5 detects a bright ring (the illumination light image 22a) and a dark ring (the phase plate image 32a) in the image for correction. Next, the control unit 5 determines the position and size of the reflected light of the DMD 22 with which the bright ring and the dark ring are concentric and the illumination light image 22a is included in the phase plate image 32a. Specifically, the control unit 5 obtains the position and size of the reflected light of the DMD 22 with which the bright ring and the dark ring are concentric by moving the position of the reflected light of the DMD 22 within a predetermined range in at least one of the X-axis direction and the Y-axis direction, and also changing the size of the reflected light of the DMD 22 within a predetermined range.

Next, the control unit 5 detects whether the illumination light image 22a is deformed in the image for correction. Then, when the illumination light image 22a is deformed, the control unit 5 obtains the shape of the reflected light of the DMD 22 with which the outer circumference and the inner circumference of the ring of the illumination light image 22a become substantially perfect circles. Specifically, the control unit 5 detects the shape of the bright ring in the image for correction. Next, the control unit 5 obtains the shape of the reflected light of the DMD 22 with which the outer circumference and the inner circumference of the bright ring become substantially perfect circles by deforming the shape of the reflected light of the DMD 22 within a predetermined range.

Then, the control unit 5 associates the information of the imaging position of the image for correction, i.e., the imaging system position information, with the information of the position, shape, and size of the reflected light of the DMD 22, which is the intensity distribution of illumination light, and stores the associated information as the intensity distribution correction information in the auxiliary storage device 53. The information to be stored in the auxiliary storage device 53 is preferably stored in association with the information on the type and size of the cell culture vessel 41 and the conditions of the imaging target such as the type and amount of the culture solution, because the intensity distribution correction information can be specified by the type and size of the cell culture vessel 41 and the conditions of the imaging target such as the type and amount of the culture solution, for example, at the time of imaging using the phase difference observation apparatus 100 to be described below.

Furthermore, the control unit 5 may detect whether there is a blurring of the illumination light image 22a. When there is blurring of the illumination light image 22a, the control unit 5 obtains the positions of the light source 1 and the illumination optical system 2 at which the blurring of the illumination light image 22a is eliminated. Specifically, the control unit 5 obtains the positions of the light source 1 and the illumination optical system 2 at which blurring of the illumination light image 22a is eliminated by moving the first moving unit 6 in the Z-axis direction within a predetermined range to move the light source 1 and the illumination optical system 2. In addition, the control unit 5 acquires the illumination system position information, which is the position of the light source 1 and the position of the illumination optical system 2 at which blurring is eliminated. The illumination system position information (the positions of the light source 1 and the illumination optical system 2) includes, for example, coordinates (three-dimensional coordinates) in the XYZ axes or a coordinate in the Z axis. Then, the control unit 5 associates the imaging system position information with the illumination system position information, which is the position of the light source 1 and the position of the illumination optical system 2 at which the blurring is eliminated, and stores the associated information as the illumination system position correction information in the auxiliary storage device 53. It is preferable that the illumination system position correction information is stored in association with the condition of the imaging target in the same manner as the intensity distribution correction information, for example.

While the control unit 5 acquires the intensity distribution correction information by correcting the entire intensity distribution of illumination light in the phase difference observation apparatus 100 of the present embodiment, the control unit 5 may acquire the intensity distribution correction information by other methods. Specifically, for example, the control unit 5 operates one DMD 22 mirror at one position of the imaging optical system 3, and reflects the illumination light toward the observation target object 42 by the operated mirror. At this time, the control unit 5 takes the image for correction by, for example, the image sensor 34. Next, for example, the control unit 5 specifies the position where the reflected light from the mirror forms an image in the image for correction, and associates the position information of the operated mirror with the imaging position of the reflected light in the image for correction. Furthermore, the control unit 5 performs this operation for all the mirrors of the DMD 22, for example, and associates the position information of each mirror with the imaging position of the reflected light in the image for correction. Then, the control unit 5 extracts the imaging position included in the phase plate image 32a from the imaging positions of the reflected light of each mirror in the image for correction. When the control unit 5 operates, on the basis of the position information of the mirror corresponding to the extracted imaging position, the mirror of the DMD 22 at the corresponding position, for example, and reflects the illumination light toward the observation target object 42 by the operated mirror, the illumination light image 22a is included in the phase plate image 32a. Therefore, for example, the control unit 5 associates the imaging system position information with the position information of the mirror corresponding to the extracted imaging position, and stores the associated information as the intensity distribution correction information in the auxiliary storage device 53. The control unit 5 performs, for example, the same treatment at the position of the other imaging optical system 3, and acquires intensity distribution correction information at the position of each imaging optical system 3.

While the present invention is described with reference to the case where the control unit 5 calculates the intensity distribution correction information, the intensity distribution correction information may be input by the user of the phase difference observation apparatus 100 using the above-mentioned input device or the like, for example, on the basis of the image for correction.

In this manner, the intensity distribution correction information can be acquired using the phase difference observation apparatus 100 of the present embodiment.

Figure 5:
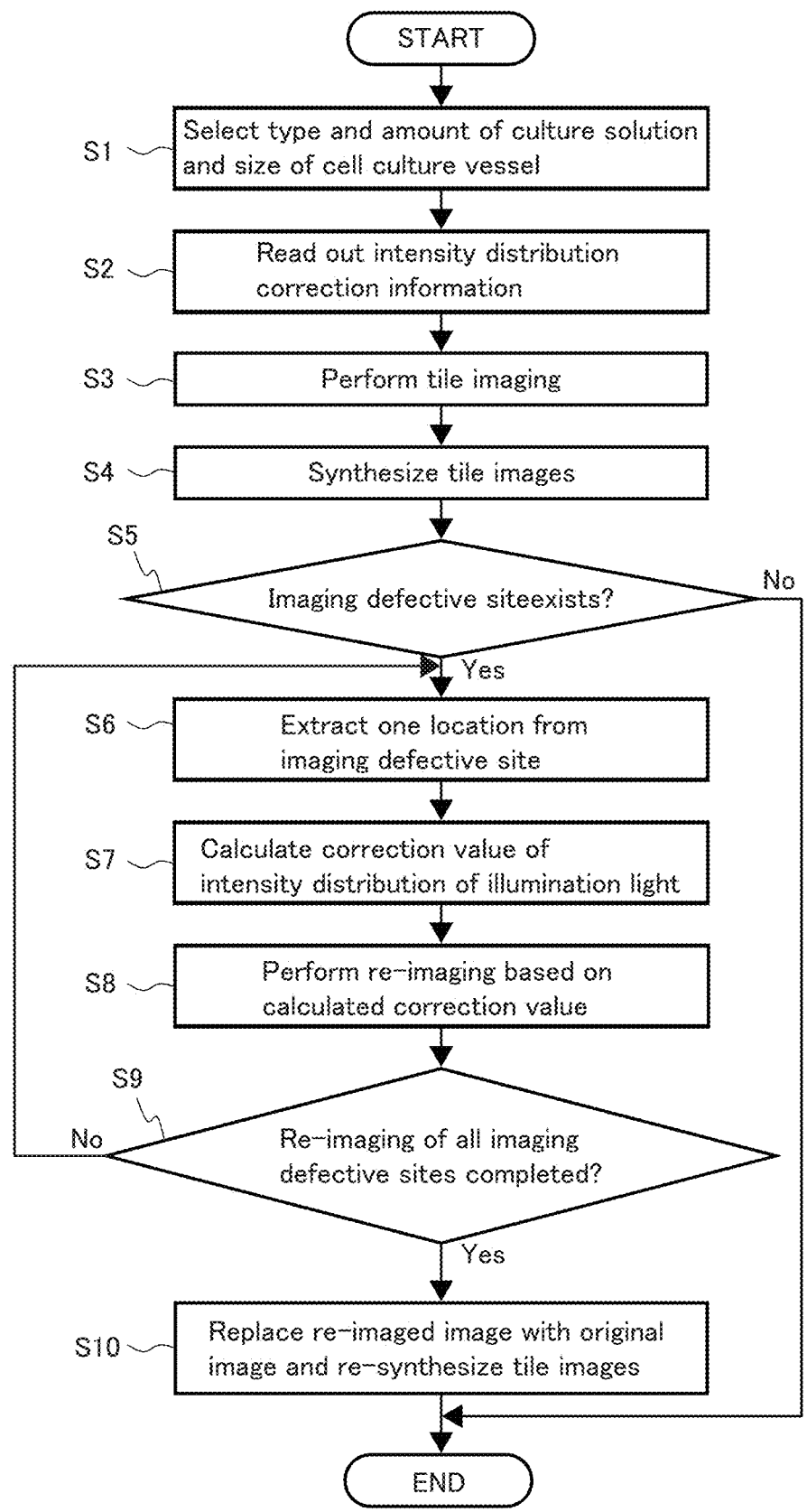
FIG. 5 is a flowchart showing an example of a method of imaging tile images of a phase difference image using the phase difference observation apparatus according to the first embodiment.

FIG. 5 is a flowchart showing a method of imaging tile images of a phase difference image using the phase difference observation apparatus 100 shown in FIG. 1. As shown in FIG. 5, the method of imaging a phase difference image using the phase difference observation apparatus 100 of the present embodiment includes, for example, steps S1 to S4. The imaging method may further include steps S5 to S10. While the method is described below with reference to the case of imaging the entire cell culture vessel 41, the region to be imaged (imaging target region) by the phase difference observation apparatus 100 is not limited thereto. The phase difference observation apparatus 100 images, for example, the imaging target region set by a user or the like. The imaging target region is, for example, a part or the entire cell culture vessel 41. The image is, for example, an image including the observation target object 42 in the cell culture vessel 41.

First, in step S1, the user of the phase difference observation apparatus 100 selects the conditions of the imaging target such as the size of the cell culture vessel 41 to be imaged, the type, amount, and the like of the culture solution in the cell culture vessel 41. Then, in step S2, the intensity distribution correction information satisfying the condition of the selected imaging target is read out from the auxiliary storage device 53. When the illumination system position correction information is stored in the auxiliary storage device 53, the illumination system position correction information may be read out from the auxiliary storage device 53.

Next, in step S3, the cell culture vessel 41 containing the observation target object 42 placed in the phase difference observation apparatus 100 is subjected to tile imaging. The control unit 5 acquires the imaging system position information, which is the position of the imaging optical system 3, at the time of imaging, and corrects the intensity distribution of illumination light on the basis of the imaging system position information and the intensity distribution correction information so as to achieve the position, shape, and size of the reflected light of the DMD 22 corresponding to the position of the imaging optical system 3. Then, the phase difference image is taken by the image sensor 34 in the phase difference observation apparatus 100. When the illumination system position correction information is read out, the control unit 5 may further correct the positions of the light source 1 and the illumination optical system 2 by moving the first moving unit 6 to the position of the first moving unit 6 corresponding to the position of the imaging optical system 3 on the basis of the imaging system position information and the illumination system position correction information. Further, the phase difference image may be taken by the image sensor 34 in the phase difference observation apparatus 100.

In step S4, the control unit 5 synthesizes the tile images on the basis of the obtained phase difference image. In this manner, tile images can be acquired using the phase difference observation apparatus 100 of FIG. 1. While the method is described with reference to the case of acquiring the tile images as an example, only the phase difference image of the region in which the observation target object 42 is present in the cell culture vessel 41 may be acquired by using the phase difference observation apparatus 100.

In the case of acquiring tile images using the phase difference observation apparatus 100 of FIG. 1, the control unit 5 may further detect an imaging defective site in the taken image used for synthesizing the tile images so that it can compensate the reduction of the phase difference effect caused by the difference between the type and amount of the culture solution and the type and size of the cell culture vessel 41 in the set intensity distribution correction information and the type and amount of the culture solution in the cell culture vessel 41 to be imaged and the type and size of the cell culture vessel 41 to be imaged. In this case, the control unit 5 calculates, as to the location (section) of the cell culture vessel 41 corresponding to the imaging defective site, the correction value of the imaging condition (correction value of the intensity distribution correction information), and performs re-imaging by the image sensor 34.

Specifically, first, in step S5, the control unit 5 detects whether there is an imaging defective site. In the case of No, the control unit 5 ends the processing. On the other hand, in the case of Yes, the process proceeds to step S6. The imaging defective site means, for example, a region in which contrast is lowered due to an increase in luminance. Specifically, the control unit 5 calculates, as to the obtained phase difference images, a total value of luminance values in one phase difference. When the obtained total value of the luminance values is equal to or more than the threshold value, the control unit 5 determines that the region is an imaging defective site. The threshold value may be a freely-determined value, and specifically, may be a value at least a predetermined multiple (e.g., at least 1.15 times) from the total value of the luminance values of the phase difference image taken in the region where the culture solution in the cell culture vessel 41 is horizontal. Detection of an imaging defective site on the basis of the total value of the luminance values is performed, for example, on the entire or a part of the obtained phase difference image. As a specific example, in the phase difference image, the stage 4 is shown as a dark part in the phase difference image, for example. Therefore, in the case of detecting the imaging defective site on the basis of the total value of the luminance values, for example, processing may be performed such that the tile images corresponding to the phase difference image including the stage 4 are excluded from the detection target of the imaging defective site on the basis of the total value of the luminance values. The tile images corresponding to the excluded phase difference image may be detected as to whether the region corresponds to an imaging defective site by, for example, another method of detecting an imaging defective site.

Next, the control unit 5 calculates a correction value at the time of re-imaging the phase difference image corresponding to the imaging defective site. The correction value may be, for example, a correction value for correcting the intensity distribution of illumination light, i.e., the position, size, and shape of the reflected light of the DMD 22, or may be a correction value for correcting the positions of the light source 1 and the illumination optical system 2. The correction value is set, for example, such that the total value of the luminance values in the re-imaged phase difference image is less than the threshold value.

When the control unit 5 calculates a correction value on the position, size, and shape of the reflected light of the DMD 22, the correction value is calculated, for example, as follows. First, in step S6, one location (one phase difference image) for calculating a correction value is extracted from the imaging defective site. In step S7, the correction values are calculated in the same manner as in the method of obtaining the position, size, and shape of the reflected light of the DMD 22 in the intensity distribution correction information.

In step S8, the control unit 5 performs re-imaging on the basis of the calculated correction value. Specifically, the control unit 5 corrects the intensity distribution of illumination light, the position, size, and shape of the reflected light of the DMD 22 on the basis of the correction values, and performs re-imaging.

Next, in step S9, the control unit 5 checks whether re-imaging of all the imaging defective sites has been completed. In the case of No, the process returns to step S6. On the other hand, in the case of Yes, the process proceeds to step S10. Then, in step S10, the control unit 5 replaces the re-imaged phase difference image (re-imaged image) of S10 with the original phase difference image, i.e., the first imaged phase difference image, and then re-synthesizes the tile images on the basis of the obtained phase difference image. Then, the control unit 5 ends the processing.

While the method of imaging tile images is described with reference to the case of calculating the correction values on the position, size, and shape of the reflected light of the DMD 22, the correction values for correcting the positions of the light source 1 and the illumination optical system 2 may be used as described above. In this case, the correction value can be calculated, for example, as follows. First, one location (one phase difference image) for calculating a correction value is extracted from the imaging defective site. Next, a correction value in the X-axis direction, a correction value in the Y-axis direction, and a correction value in the Z-axis direction of the light source 1 and the illumination optical system 2 (illumination system) are calculated. Specifically, the control unit 5 moves the positions of the light source 1 and the illumination optical system 2 in the X-axis direction, the Y-axis direction, and/or the Z-axis direction within a predetermined range by the first moving unit 6. At this time, in parallel with the movement, the control unit 5 calculates the total value of the luminance values in the phase difference image taken by the image sensor 34. Then, the control unit 5 calculates, as a correction value, a position at which the total value of the luminance values in each phase difference image is equal to or less than the threshold value, preferably, a position at which the total value becomes the minimum value. The position is, for example, a coordinate (three-dimensional coordinate) in the XYZ axes.

Figure 6:
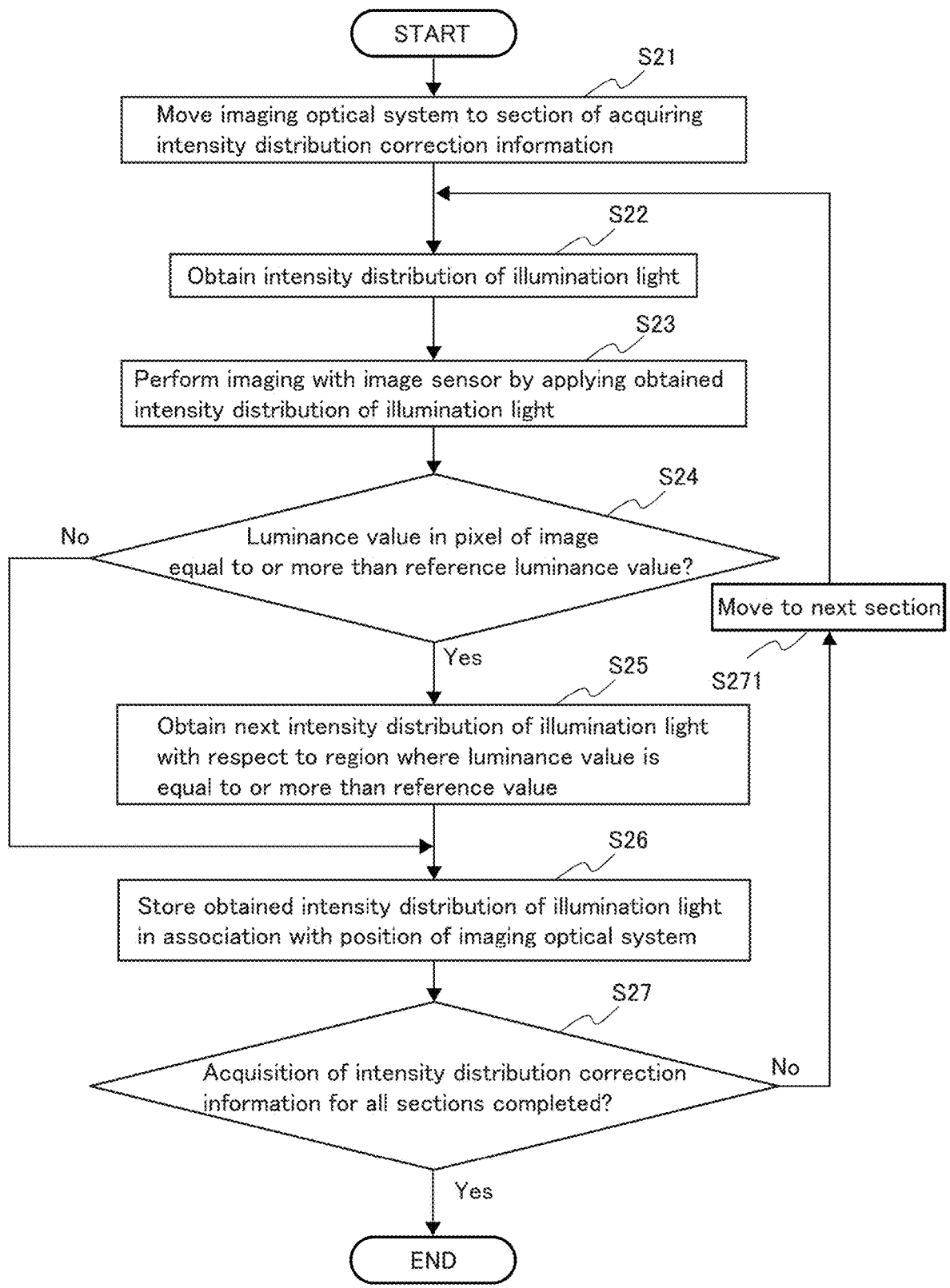
FIG. 6 is a flowchart showing another example of the method of acquiring intensity distribution correction information in the method of imaging tile images of a phase difference image using the phase difference observation apparatus according to the first embodiment.

In the imaging method using the phase difference observation apparatus 100, in step S3, the images may be taken using a plurality of intensity distributions of illumination light for one section, and the image among the obtained images suitable as the phase difference image may be used to produce the image of one section. That is, the intensity distribution correction information for one section may include a plurality of intensity distributions of illumination light. FIG. 6 is a flowchart showing another example of a method of acquiring intensity distribution correction information including one or more intensity distributions of illumination light using the phase difference observation apparatus 100 of FIG. 3. As shown in FIG. 6, the method of acquiring intensity distribution correction information includes steps S21 to S27 and step S271. The acquisition of the intensity distribution correction information is performed prior to step S1, for example.

First, in step S21, the imaging optical system 3 is moved to a section of acquiring intensity distribution correction information. Next, in step S22, in the above-mentioned section, the control unit 5 obtains the intensity distribution of illumination light (the first intensity distribution of illumination light) with which the illumination light image 22a is included in the phase plate image 32a. That is, the control unit 5 obtains the position information of the mirror of the DMD 22 that reflects the illumination light toward the observation target object 42 when the intensity distribution of illumination light is corrected such that the illumination light image 22a is included in the phase plate image 32a, and the position information of the mirror of the DMD 22 that does not reflect the illumination light toward the observation target object 42. More specifically, as described above, the control unit 5 obtains the position and size of the reflected light of the DMD 22 with which the illumination light image 22a is included in the phase plate image 32a.

Next, in step S23, the control unit 5 changes the intensity distribution of illumination light in the DMD 22 with the intensity distribution of illumination light obtained in step S22, and images the section by the image sensor 34. In step S24, it is determined whether the luminance value in the pixel of the obtained image is equal to or more than a reference luminance value. While the pixel may be one pixel or a plurality of pixels in the image, the latter is preferable because a change in luminance value can be easily detected and an influence due to the meniscus can be suppressed. In the latter case, the pixels may also be referred to as pixel blocks. The pixel block can be produced, for example, by dividing the image into a plurality of units with a freely selected number of adjacent pixels in the image as one unit. As a specific example, the pixel block can be produced, for example, by dividing the image into squares. When the pixel is a pixel block, the luminance value of the pixel can be calculated, for example, as the total value of the luminance values of the pixels of the pixel block. The reference luminance value can be any value, and for example, the reference value is set such that the obtained image includes a pixel whose luminance value reaches the upper limit value. As a specific example, the reference value ($B_s$) of the luminance value is, for example, $1.1 \times B_L \leq B_s \leq 1.2 \times B_L$, preferably $B_s = 1.15 \times B_L$, with reference to the lowest luminance value ($B_L$) in the pixels of the images. Then, in the case of No, that is, in the case where the luminance value in the image is less than the reference luminance value, the process proceeds to step S26. On the other hand, in the case of Yes, that is, in the case where the luminance value in the image is equal to or more than the reference luminance value, in step S25, in the above-mentioned section, the control unit 5 changes the illumination light image 22a with respect to the region where the luminance value of the image is equal to or more than the reference value, and obtains next intensity distribution of illumination light (the second intensity distribution of illumination light). The illumination light image 22a may be changed so as to be included in the phase plate image 32a, or so as not to be included in the phase plate image 32a partially or as a whole, for example. The change of the illumination light image 22a is preferably performed by, for example, moving the position of the illumination light image 22a. In this case, it is preferable that the size and shape of the illumination light image 22a are not changed. For example, the phase difference observation apparatus 100 can suppress an increase in the luminance value due to direct incidence of the illumination light by moving the position of the illumination light image 22a. Thus, the phase difference observation apparatus 100 can obtain the intensity distribution of illumination light with which the phase difference image of the observation target object 42 with an appropriate contrast can be obtained in a region in which the luminance value in the image is equal to or more than a reference value, for example.

In step S26, the first and second intensity distributions of illumination light are associated with the position of the imaging optical system 3 and stored as the intensity distribution correction information. In step S26, for example, each intensity distribution of illumination light may be associated with a region in which the luminance value in the image is equal to or more than a reference value and stored as the intensity distribution correction information. Thereby, the phase difference observation apparatus 100 can easily acquire the image of the above-mentioned section by integrating the regions in which the luminance value in the image is less than a reference value after imaging by the image sensor 34, for example. While the process proceeds to step S26 after step S25 in the description of the acquisition method in the imaging method of the present embodiment, the process may return to step S23 again, and the process from step S23 may be performed in the same manner using the second intensity distribution of illumination light instead of the first intensity distribution of illumination light. In this case, steps S24 and S25 are performed with respect to a region (a region before correction) in which the luminance value in the image is equal to or more than a reference value when imaging is performed by applying the first intensity distribution of illumination light among images obtained by applying the second intensity distribution of illumination light. The same steps may be repeatedly performed until the luminance value in the pixel in the region of each of the images before correction obtained with the first and second intensity distributions in step S23 becomes less than the reference luminance value. That is, the imaging method of the present embodiment may be performed until an image of the entire section of the imaging target is obtained when integrating the regions in which the luminance value in the image is less than a reference value in the images obtained with the first and second intensity distributions.

In step S27, it is determined whether the acquisition of the intensity distribution correction information for all the sections has been completed. In the case of No, that is, in the case where the acquisition of the intensity distribution correction information for all the sections has not been completed, the imaging optical system 3 is moved to the next section in step S271, and step S22 is performed again. On the other hand, in the case of Yes, that is, in the case where the acquisition of the intensity distribution correction information for all the sections has been completed, the acquisition method of the intensity distribution correction information is terminated.

Figure 7:
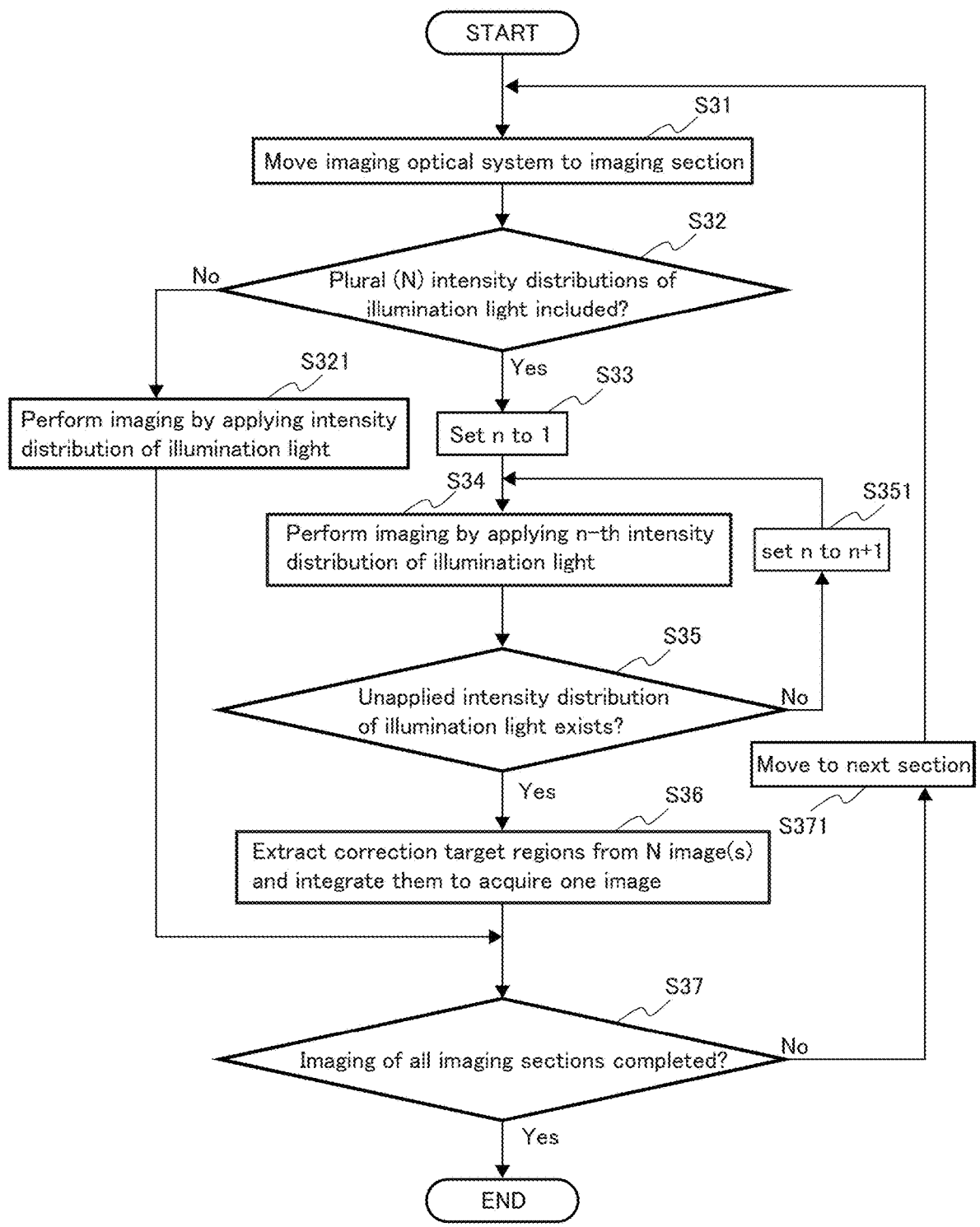
FIG. 7 is a flowchart showing another example of step S3 in the method of imaging tile images of a phase difference image using the phase difference observation apparatus according to the first embodiment.

Next, an imaging method using the intensity distribution correction information obtained by the acquisition method and the phase difference observation apparatus 100 is described below. FIG. 7 is a flowchart showing another example of step S3 in the method of imaging tile images of a phase difference image using the phase difference observation apparatus 100 shown in FIG. 1. As shown in FIG. 7, step S3 includes, for example, steps S31 to S37, step S321, step S351, and step S371.

First, in step S31, the imaging optical system 3 is moved to an imaging section. Next, in step S32, the intensity distribution correction information corresponding to the section, that is, the intensity distribution correction information associated with the position of the imaging optical system 3 is acquired, and it is determined whether the intensity distribution correction information includes a plurality of intensity distributions of illumination light. In the case of No, that is, in the case where the intensity distribution correction information includes one intensity distribution of illumination light, in step S321, the intensity distribution of illumination light in the DMD 22 is changed to the intensity distribution of illumination light obtained in step S32, the section is imaged by the image sensor 34, and the process proceeds to step S37. On the other hand, in the case of Yes, that is, in the case where the intensity distribution correction information includes a plurality of intensity distributions of illumination light, the process proceeds to step S33. Hereinafter, a case where there are a plurality (N times) of intensity distributions of illumination light will be described as an example. N indicates an integer of 2 or more. In step S33, the number n of times of the intensity distribution of illumination light applied at the time of imaging is set to 1. Next, in step S34, the intensity distribution of illumination light in the DMD 22 is changed to the first intensity distribution of illumination light, and the section is imaged by the image sensor 34.

After the imaging, it is determined whether there is an intensity distribution of illumination light that is not applied among N-th of the intensity distributions of illumination light. That is, it is determined whether N=n. Then, in the case of No, that is, in the case of N≠n, n is set to n+1 (in this case, n=2) in step S351, and the process returns to step S34. Then, the process from step S34 is performed in the same manner by applying the second intensity distribution of illumination light. In the imaging method, steps S34 and S35 are repeatedly performed until N=n is satisfied. On the other hand, in the case of Yes, that is, in the case of N=n, a region (correction target region) in which the luminance value in the pixels of the obtained N images is less than the reference luminance value is extracted, and the extracted images are integrated. In step S36, one image of the section is acquired.

Then, in step S37, it is determined whether the imaging has been completed for all the sections. In the case of No, in step S371, the process moves to the next section, and the process from step S32 is performed in the same manner. On the other hand, in the case of Yes, step S3 is terminated.

In step S3, by applying intensity distribution correction information including one or more intensity distributions of illumination light and taking an image, an image can be obtained while suppressing the deterioration of the phase difference image even in a case where it is difficult to obtain such an image with only a correction on the basis of the intensity distribution correction information including one intensity distribution of illumination light in one section.

According to the phase difference observation apparatus 100 of the present embodiment, an additional imaging unit for suppressing deterioration of a phase difference image due to the meniscus as required in Patent Literature 1 is unnecessary. Therefore, according to the phase difference observation apparatus 100 of the present embodiment, the size of the apparatus can be reduced. Furthermore, since the phase difference observation apparatus 100 of the present embodiment corrects the intensity distribution of illumination light at the time of imaging on the basis of the intensity distribution correction information acquired by using the cell culture vessel 41 containing no observation target object 42, for example, imaging can be performed in a shorter time as compared to the apparatus of Patent Literature 1 that performs correction by calculating a correction value at the time of imaging. In addition, since the phase difference observation apparatus 100 of the present embodiment corrects the intensity distribution of illumination light at the time of imaging on the basis of the intensity distribution correction information, degradation of the phase difference image due to the meniscus can be suppressed. Therefore, according to the phase difference observation apparatus 100 of the present embodiment, a phase difference image having a large contrast can be taken. These effects are the same in the cell treatment apparatus described below.

Second Embodiment

Figure 8:
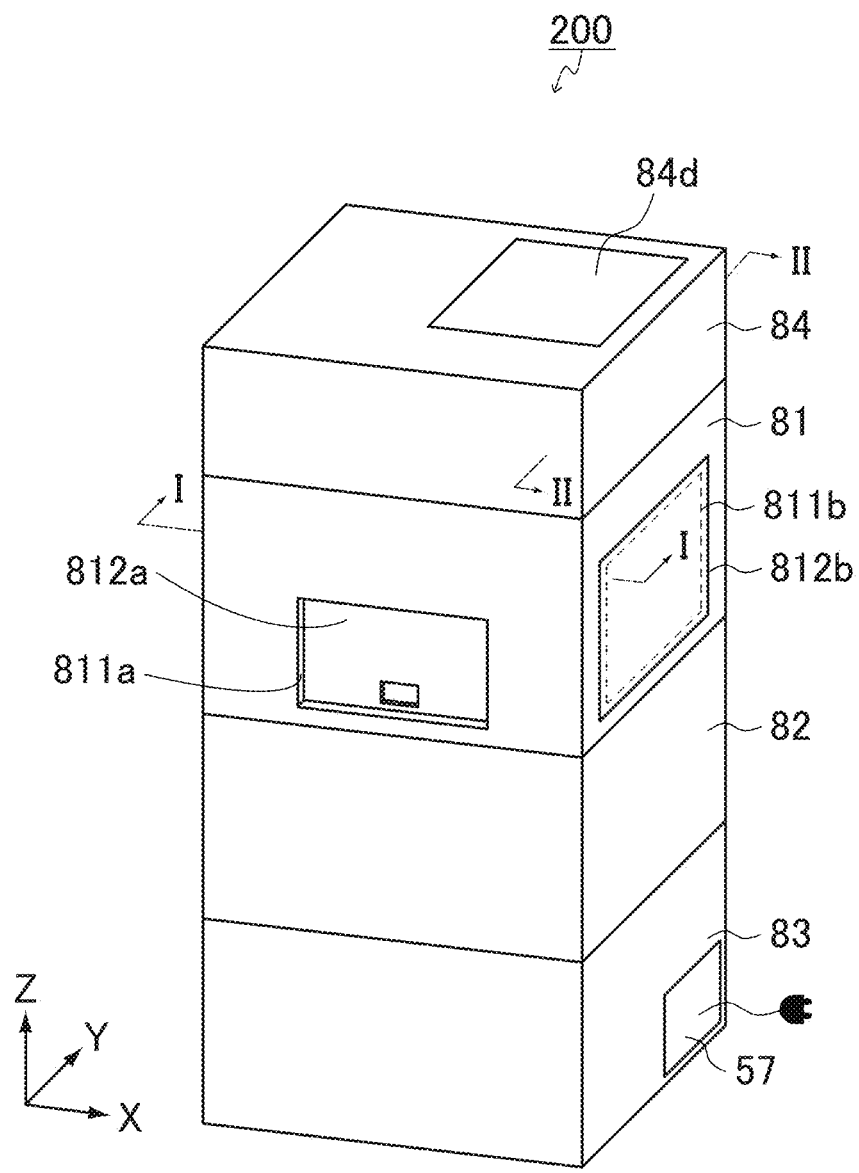
FIG. 8 is a perspective view showing an example of the cell treatment apparatus according to the second embodiment.
Figure 9:
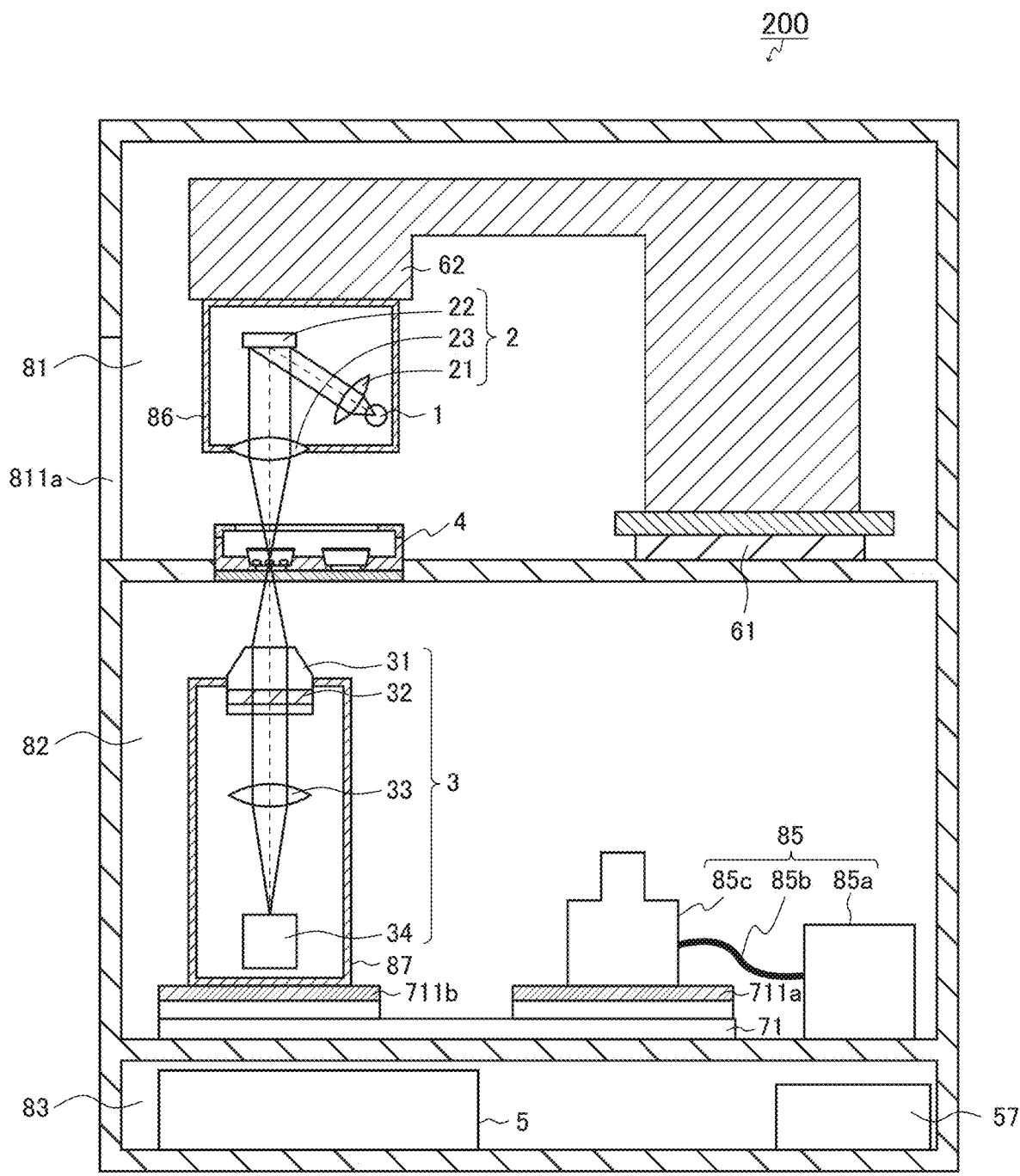
FIG. 9 is a schematic view showing an example of the cell treatment apparatus according to the second embodiment.
Figure 10:
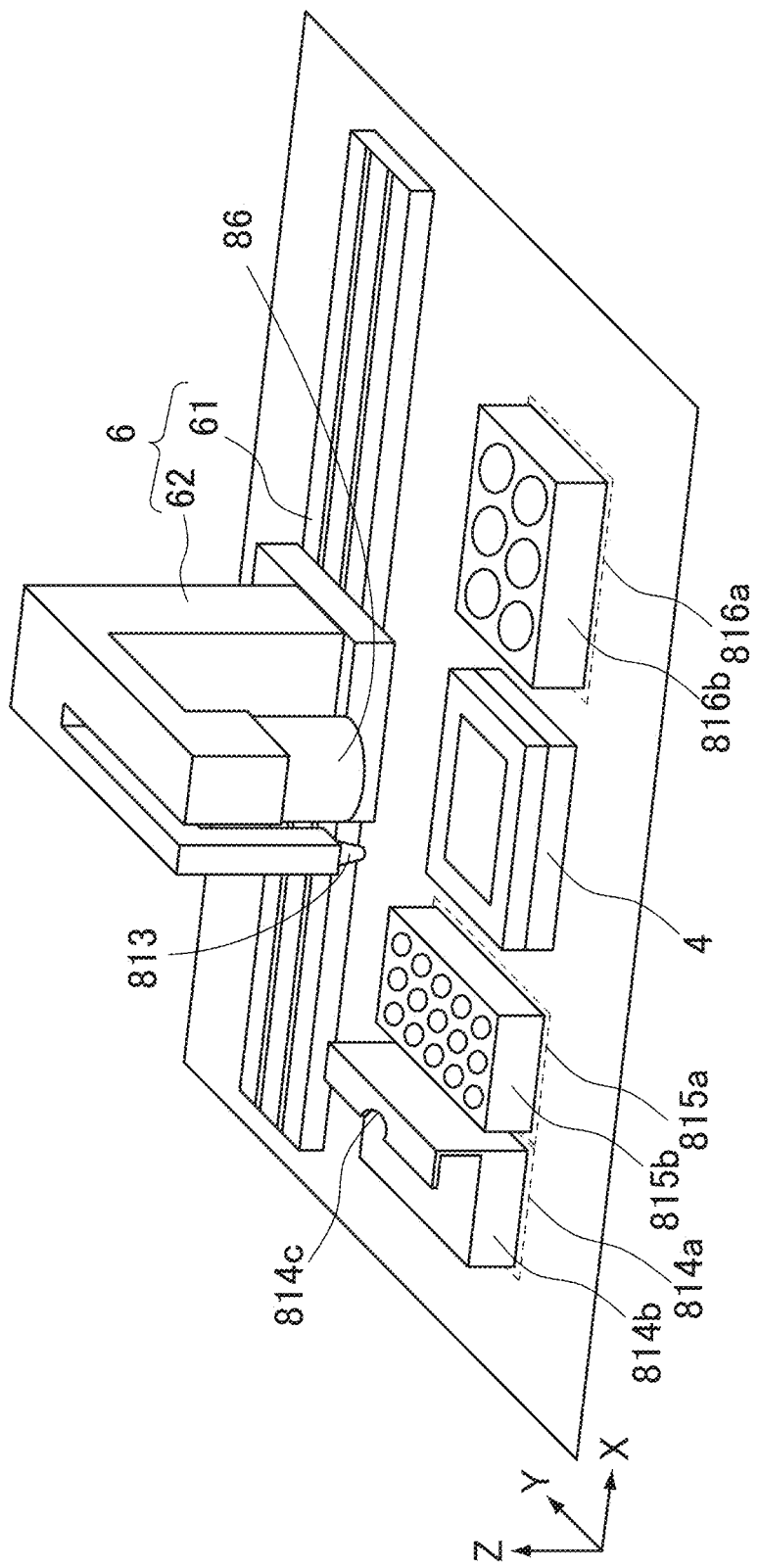
FIG. 10 is a perspective view showing an example of the first region in the cell treatment apparatus according to the second embodiment.
Figure 11:
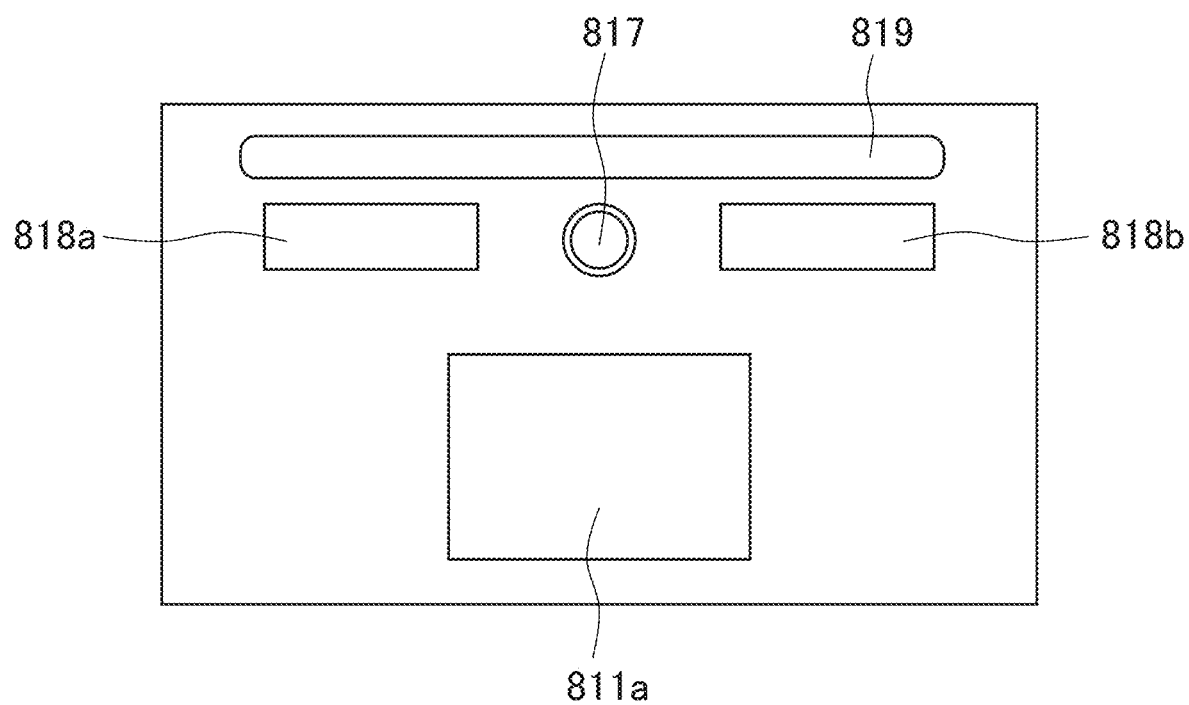
FIG. 11 is a cross-sectional view of the first region taken along the line 1-1 in FIG. 8.
Figure 12A:
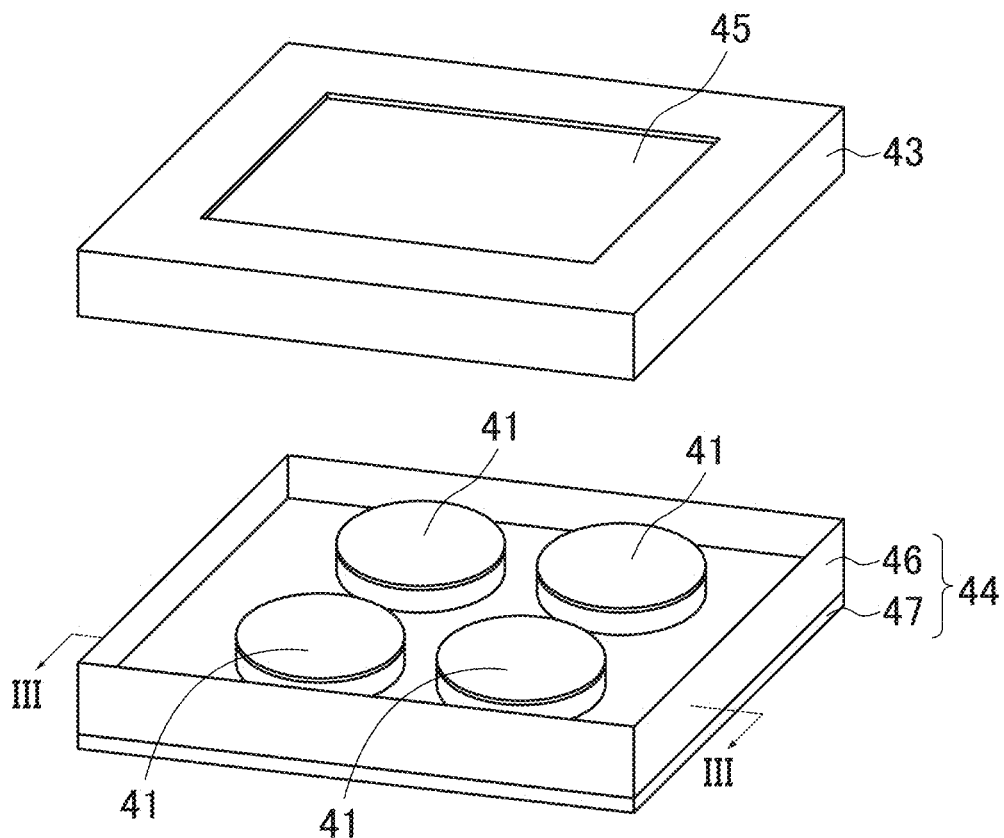
FIG. 12A is an exploded perspective view showing an example of the culture vessel placement unit in the cell treatment apparatus according to the second embodiment.
Figure 12B:
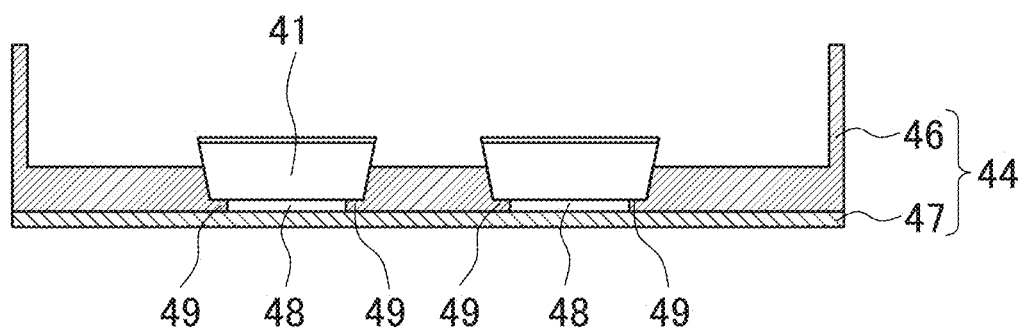
FIG. 12B is a cross-sectional view taken along the line III-III in FIG. 12A.
Figure 13:
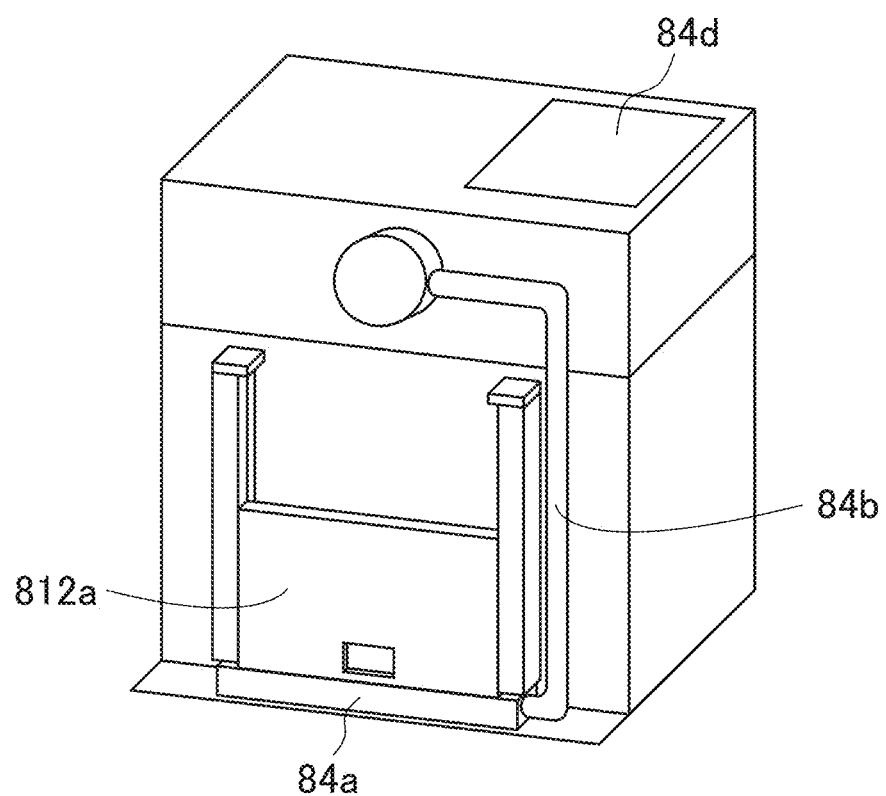
FIG. 13 is a perspective view showing an example of the first region and the circulator when the outer wall of the first region is removed in the cell treatment apparatus according to the second embodiment.
Figure 14:
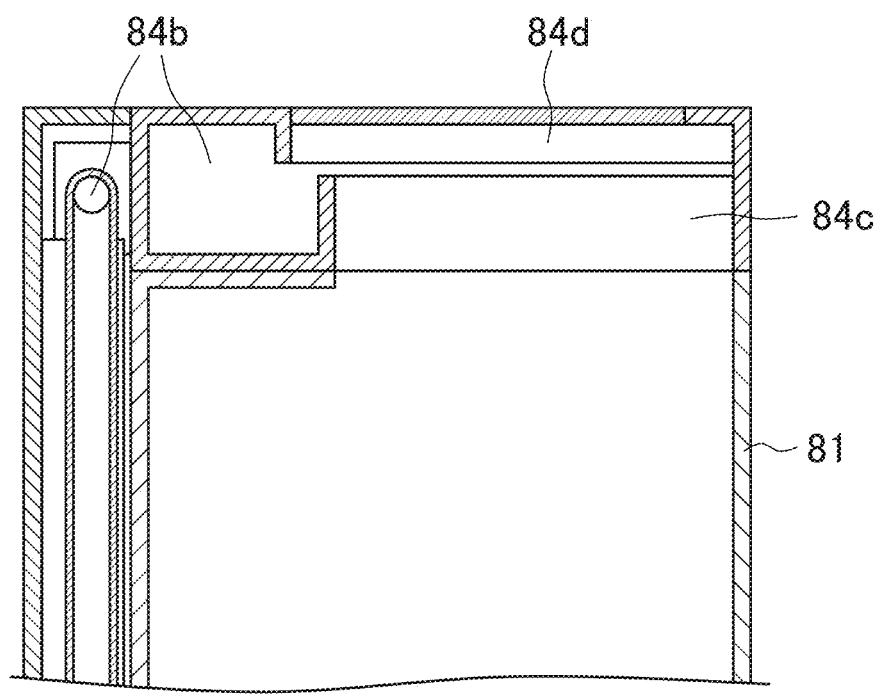
FIG. 14 is a cross-sectional view showing an upper part of the first region and the circulator taken along the line 11-11 in FIG. 8.
Figure 15A:
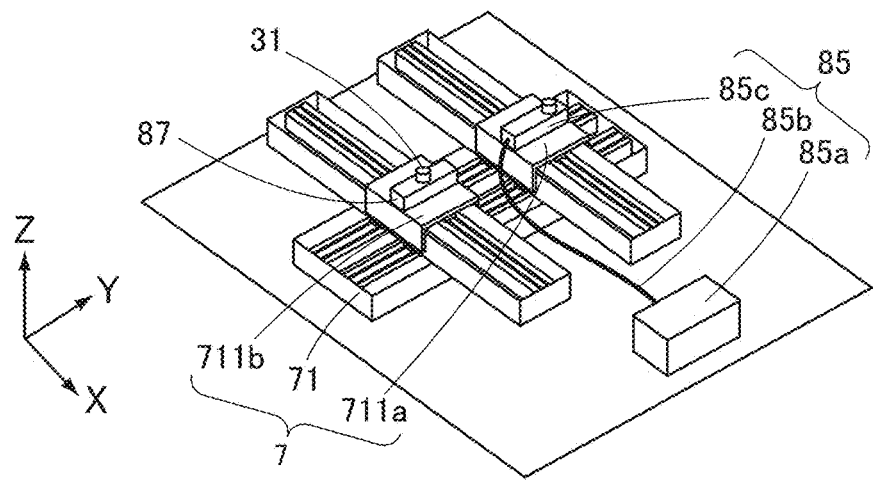
FIG. 15A is a perspective view showing an example of the configuration of the second region in the cell treatment apparatus according to the second embodiment.
Figure 15B:
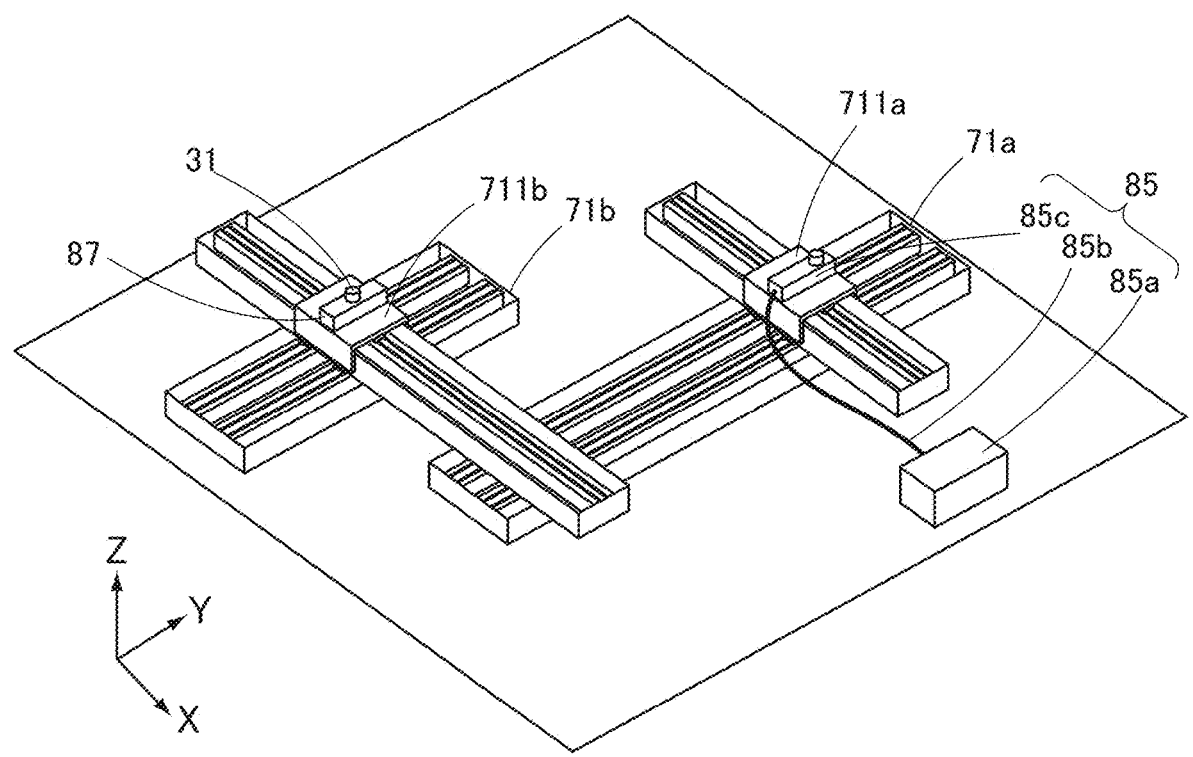
FIG. 15B is a perspective view showing another example of the configuration of the second region.
Figure 16:
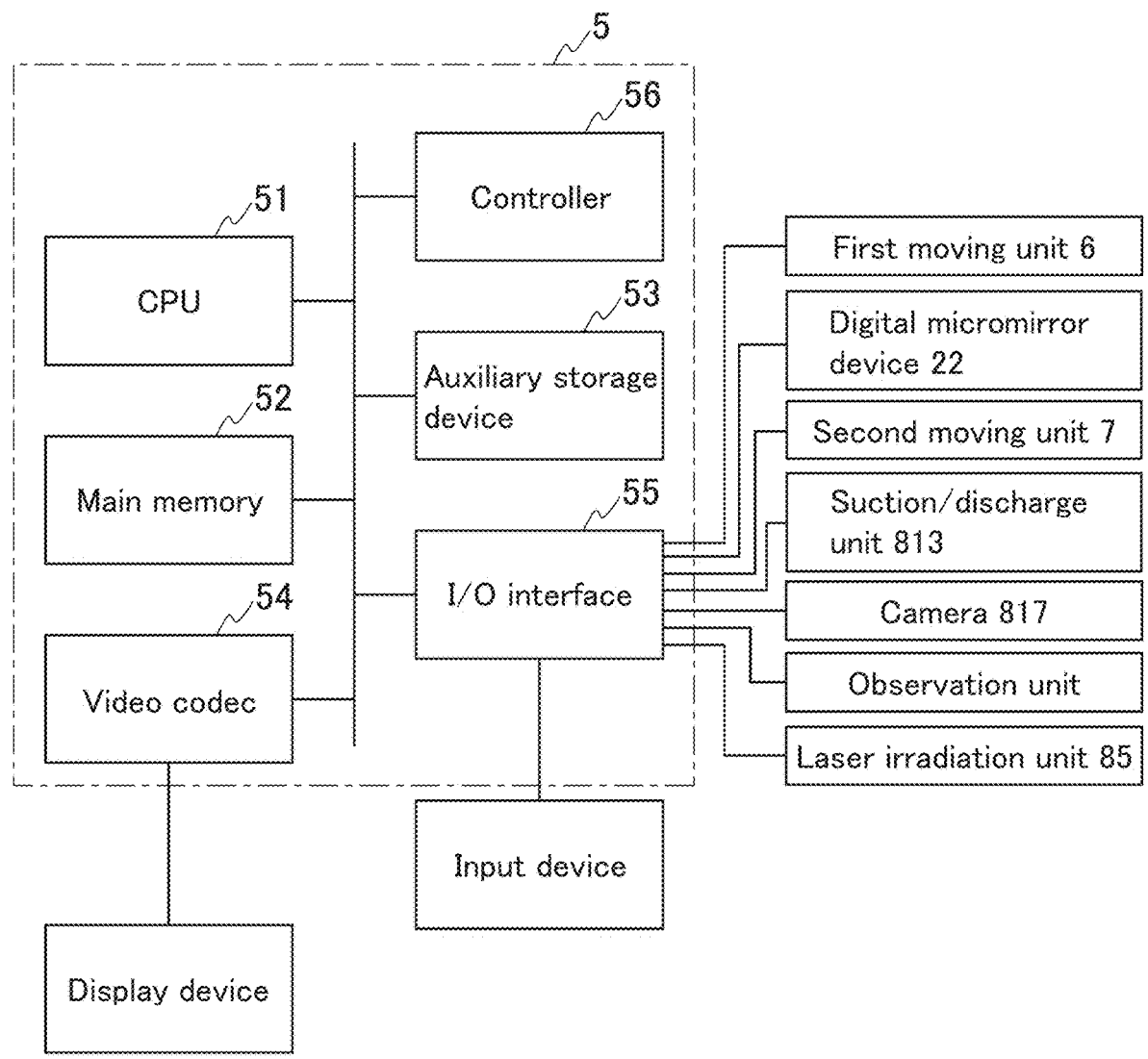
FIG. 16 is a block diagram showing an example of the configuration of the control unit of the cell treatment apparatus according to the second embodiment.
Figure 17:
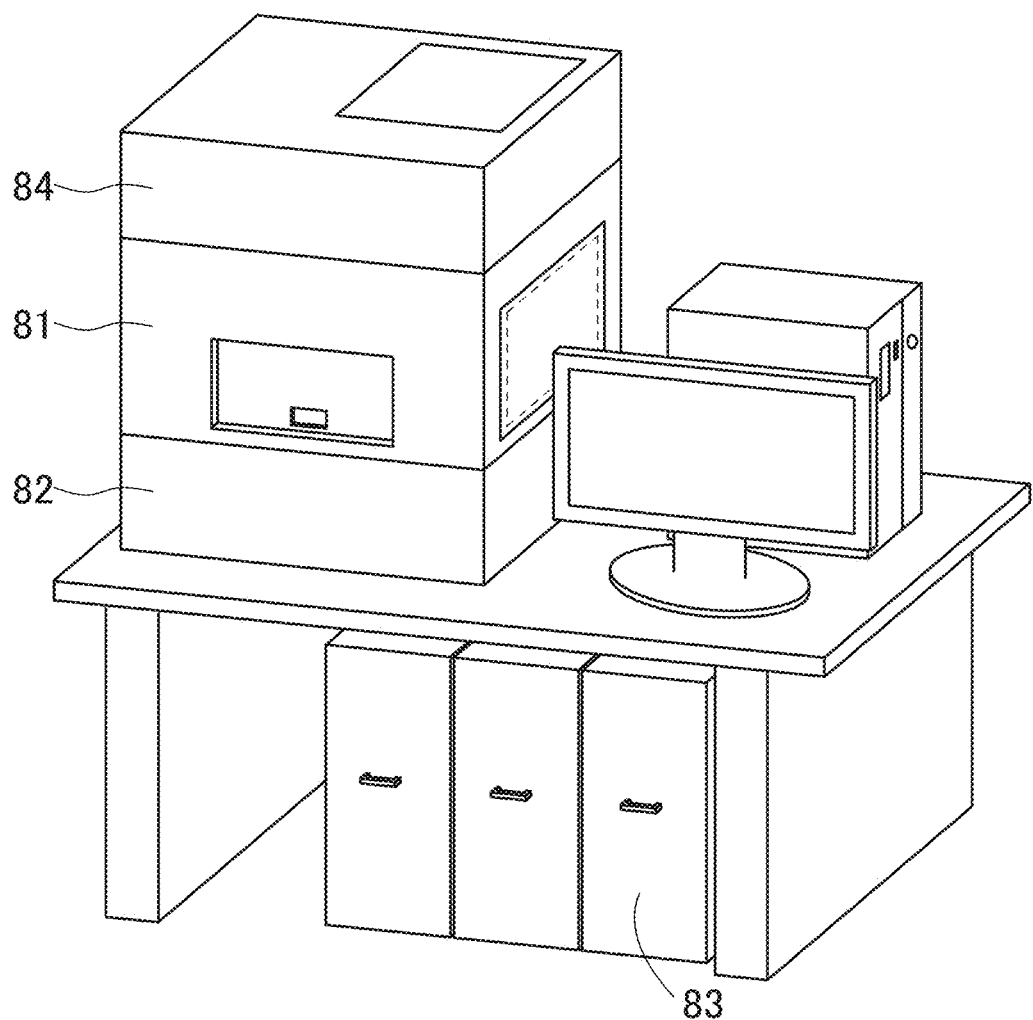
FIG. 17 is a perspective view showing another example of the cell treatment apparatus according to the second embodiment.

The present embodiment relates to an example of a cell treatment apparatus. Each of FIGS. 8 to 17 shows an example configuration of the cell treatment apparatus according to the present embodiment. FIG. 8 is a perspective view showing an example configuration of the cell treatment apparatus according to the present embodiment, FIG. 9 is a schematic cross-sectional view showing the configurations of the first region, the second region, and the third region in the cell treatment apparatus according to the present embodiment, FIG. 10 is a perspective view showing an example configuration of the first region in the cell treatment apparatus according to the present embodiment, FIG. 11 is a cross-sectional view of the first region taken along the line I-I in FIG. 8, FIG. 12A is an exploded perspective view showing an example of the culture vessel placement portion in the cell treatment apparatus according to the present embodiment, FIG. 12B is a cross-sectional view taken along the line III-III in FIG. 12A, FIG. 13 is a perspective view of the first region and the circulator when the outer wall of the first region is removed, FIG. 14 is a cross-sectional view of the upper part of the first region and the circulator taken along the line II-II in FIG. 8, FIG. 15A is a perspective view showing an example configuration of the second region in the cell treatment apparatus according to the present embodiment, FIG. 15B is a perspective view showing another example configuration of the second region, FIG. 16 is a block diagram showing an example of the control unit in the cell treatment apparatus according to the present embodiment, and FIG. 17 is a perspective view showing another example configuration of the cell treatment apparatus according to the present embodiment.

As shown in FIG. 8, the cell treatment apparatus 200 according to the present embodiment includes a first chamber 81 as the first region, a second chamber 82 as the second region, a third chamber 83 as the third region, and a circulator 84, and the first chamber 81, the second chamber 82, and the third chamber 83 are placed in this order continuously from the top downward. While the cell treatment apparatus 200 according to the present embodiment includes the circulator 84, the circulator 84 is optional, and the cell treatment apparatus 200 may or may not include the circulator 84. As to the positional relationship among the first chamber 81, the second chamber 82, and the third chamber 83, it is only required that the first chamber 81 and the second chamber 82 are placed contiguously (adjacent to each other), and the third chamber 83 may be placed at any position. The third chamber 83 may be placed separately from the first chamber 81 and the second chamber 82, for example, as shown in FIG. 17. When the third chamber 83 is placed separately from the first chamber 81 and the second chamber 82 as shown in FIG. 17, the cell treatment apparatus 200 may be also referred to as, for example, a cell treatment system. The cell treatment system may, for example, be a tabletop system. The first chamber 81 is preferably placed above the second chamber 82. When the cell culture vessel 41 is irradiated with lasers from above by the laser irradiation unit 85 described below, it is necessary to place the emission port of the laser emission portion 85c in the culture medium in the cell culture vessel 41 in order to stabilize the focal position of the laser irradiation unit 85. However, when the laser irradiation is performed in this state, a problem arises in that the components of the culture medium burn and adhere to the emission port of the laser emission portion 85c, which causes contamination of the emission port of the laser emission portion 85c. Thus, contamination of the laser emission port of the laser irradiation unit 85 can be prevented by placing the members as in the cell treatment apparatus 200 according to the present embodiment when the cells in the cell culture vessel 41 are irradiated by the laser irradiation unit 85 to be described below, for example. Therefore, the cell treatment apparatus 200 according to the present invention can stabilize the output of the laser emitted from laser irradiation unit 85 and can efficiently treat cells, for example. The material for forming each region (each chamber) is not particularly limited, and examples thereof include a stainless steel plate, a rust-proof iron plate, and a resin plate that can be molded by vacuum molding, injection molding, pressure molding, or the like. The material for forming each region is preferably a non-translucent material so that the cells in the cell culture vessel 41 can be imaged more clearly by the observation unit to be described below. The term "non-translucent" means, for example, to suppress transmission of light having a wavelength that affects imaging by the observation unit. When the observation unit can perform fluorescent observation, the wavelength of the light may be, for example, a wavelength corresponding to the fluorescence to be detected. As a specific example, the non-translucent material can be, for example, the above-mentioned material for forming each region. The size and shape of each region are not particularly limited, and can be appropriately determined depending on the size and shape of a member (unit) placed in each region. In the cell treatment apparatus 200 according to the present embodiment, the first chamber 81 and the second chamber 82 are configured by separate housings, and the housing configuring the first chamber 81 and the housing configuring the second chamber 82 are placed adjacent to each other. The present invention, however, is not limited thereto, and the first chamber 81 and the second chamber 82 may be configured by a single housing and the first chamber 81 and the second chamber 82 may be separated in the single housing. In the cell treatment apparatus 200 according to the present embodiment, the first chamber 81 and the second chamber 82 are configured by separate housings. Thus, for example, each member in the cell treatment apparatus 200 can be maintained easily, and the cell treatment apparatus 200 can be assembled easily.

Next, as shown in FIG. 9, the cell treatment apparatus 200 according to the present embodiment includes, as main components, an observation unit including, as main components, a light source 1, an illumination optical system 2, an imaging optical system 3, a cell culture vessel placement unit 4, a control unit 5, a first moving unit 6 and a second moving unit 7 to be described below, and a laser irradiation unit 85. The configuration of the observation unit other than the cell culture vessel placement unit 4 is the same as that of the phase difference observation apparatus 100 of the first embodiment, and reference can be made to the description of the first embodiment. The outer wall of the double wall of the first chamber 81 to be described below is not shown in FIG. 9. The laser irradiation unit 85 includes a laser light source 85a, an optical fiber 85b, and a laser emission portion 85c, and the laser light source 85a and the laser emission portion 85c are optically connected by the optical fiber 85b. In the first chamber 81, the light source 1 and the illumination optical system 2 accommodated in the housing 86, and the first moving unit 6 are placed. The housing 86 accommodating the light source 1 and the illumination optical system 2 is movable by the first moving unit 6. The imaging optical system 3 accommodated in a housing 87, the second moving unit 7, and the laser irradiation unit 85 are placed in the second chamber 82. The imaging optical system 3 and the laser emission portion 85c in the laser irradiation unit 85 are movable by the second moving unit 7. The control unit 5 and the power supply unit 57 are placed in the third chamber 83. The cell culture vessel placement unit 4 is formed as a part of a partition wall between the first chamber 81 and the second chamber 82. While the cell treatment apparatus 200 according to the present embodiment includes the cell culture vessel placement unit 4, the cell culture vessel 41, the first moving unit 6, the second moving unit 7, the housing 86, the housing 87, the first chamber 81, the second chamber 82, and the third chamber 83, these members are optional and the cell treatment apparatus 200 may or may not include them.

The first chamber 81 includes a work opening 811a on its front (frontward in FIG. 8) and a maintenance opening 811b for maintenance on its side. The opening 811a is a work opening for working on treatment of an observation target object in the observation target object treatment chamber as the first chamber 81. The opening 811b is a maintenance opening through which the observation target object treatment chamber can be maintained. The area of the opening 811a is preferably smaller than that of the opening 811b so that the maintenance operation is facilitated, for example. The size and number of the openings 811a and 811b are not particularly limited, and reference can be made, for example, to the size and number of the work openings and the maintenance openings in the safety cabinet. As a specific example, regarding the size and number of the openings 811a and 811b, reference can be made, for example, to the safety cabinet standard specified in EN12469:2000, which is the EN standard. The number of the openings 811b is not particularly limited and any number of openings 811b can be provided. Preferably, two or more openings 811b are provided so that maintenance is facilitated, for example. The locations of the opening 811a and the opening 811b in the first chamber 81 are not particularly limited and the opening 811a and the opening 811b can be provided at any location. Preferably, the opening 811a and the opening 811b are placed at different locations (for example, at different side surfaces) of the first chamber 81. While the opening 811b is primarily intended to facilitate maintenance in the cell treatment apparatus 200 in the present embodiment, the opening 811b may be used for other purposes. The cell treatment apparatus 200 according to the present embodiment, for example, enables observation of movement and the like of each of inside members through the opening 811b, thereby allowing direct observation of a defect site when a problem occurs in the cell treatment apparatus 200. Thus, the problem can be handled appropriately.

The front wall of the first chamber 81 is a double wall having an outer wall and an inner wall, and a door 812a opens and closes the opening 811a by moving up and down along a rail placed in the space between the outer wall and the inner wall. The opening 811b can be opened and closed by detaching and attaching the door 812b covering the opening 811b. For example, when cells are treated in the observation target object treatment chamber, the opening 811b is preferably sealed with the door 812b. Thus, for example, the gas outside the cell treatment apparatus 200 and the dust contained in the gas can be prevented from flowing into the observation target object treatment chamber. In the cell treatment apparatus 200 according to the present embodiment, the opening 811a and the door 812a thereof, and the opening 811b and the door 812b thereof are optional, the cell treatment apparatus 200 may or may not include them, and may include only either of the openings and the doors. The wall of the first chamber 81 may a double door or a single door, and the former is preferable because the size of the cell treatment apparatus 200 can be reduced by placing other members inside the double wall in the first chamber 81. When the wall of the first chamber 81 is a single wall, the door 812a is placed outside the first chamber 81, for example, like the door 812b. The type of opening and closing of the door is not particularly limited, and may be, for example, a lifting type such as the door 812a, an external type such as the door 812b, or other types. Examples of the other type include a double-door type, an accordion type, and a pull door type. The material for forming the door is not particularly limited, and, for example, the above-mentioned material for forming each region can be used, and a non-translucent material is preferable.

As shown in FIG. 10, the inside of the first chamber 81 of the cell treatment apparatus 200 according to the present embodiment is an observation target object treatment chamber for treating an observation target object and can be closed by closing the doors 812a and 812b, that is, is openable and closable. The observation target object treatment chamber includes: a first moving unit 6 having an XY stage 61 and an arm 62; a suction/discharge unit 813; a housing 86 accommodating an illumination optical system 2; a drainage container placement portion 814a; a storage container placement portion 815a; a cell culture vessel placement unit 4; and a collection container placement portion 816a. While the observation target object treatment chamber includes the first moving unit 6 including the XY stage 61 and the arm 62, the suction/discharge unit 813, the drainage container placement portion 814a, the storage container placement portion 815a, and the collection container placement portion 816a in the present embodiment, these members are optional and the observation target object treatment chamber may or may not include any one or more of them. The XY stage 61 is placed on the bottom surface of the observation target object treatment chamber and is placed so as to be movable in the X-axis direction and the Y-axis direction. The arm 62 having a pair of arms is placed on the XY stage 61. At the end of one of the arms in the arm 62, the suction/discharge unit 813 is placed with its suction/discharge port face downward. Further, at the end of the other arm in the arm 62, the housing 86 accommodating the illumination optical system 2 is placed so as to be able to guide (emit) illumination light toward observation target object 42. The drainage container placement portion 814a, the storage container placement portion 815a, the cell culture vessel placement unit 4, and the collection container placement portion 816a are placed on the bottom surface of the observation target object treatment chamber in this order along the moving direction of the XY stage 61 in the X-axis direction. A drainage container 814b including a tip member detachment unit 814c is placed in the drainage container placement portion 814a, a storage container 815b is placed in the storage container placement portion 815a, and a collection container 816b is placed in the collection container placement portion 816a.

While the cell treatment apparatus 200 according to the present embodiment can move the illumination optical system 2 and the suction/discharge unit 813 by the XY stage 61 and the arm 62, which are collectively the first moving unit 6, the suction/discharge unit 813 may be moved by a drive unit other than the first moving unit 6. In this case, the moving direction of the drive unit that can move the suction/discharge unit 813 is not particularly limited, and is, for example, any one direction, two directions, or all directions of the X-axis direction, the Y-axis direction, and the Z-axis direction. In the present embodiment, the XY stage 61 is a known stage that can move an object at high speed and accurately along the X-axis direction and the Y-axis direction through a linear motor carriage or the like, for example. While the arm 62 is extendable in the vertical direction (Z-axis direction), the arm 62 may be fixed. In the latter case, the first moving unit 6 can move the suction/discharge unit 813 only on the XY plane, that is, only in the X-axis direction and the Y-axis direction in FIG. 10.

The suction/discharge unit 813 sucks and discharges, for example, the culture medium, the cells, and the like in the cell culture vessel 41. The suction/discharge unit 813 is used, for example, by mounting a tip member to be described below on its suction/discharge port side. The suction/discharge unit 813 is not particularly limited, and, for example, a known suction/discharge unit can be used. Specific examples thereof include an electric pipettor and an electric syringe pump.

The drainage container placement portion 814a is a region where a drainage container 814b for draining a liquid sucked by the suction/discharge unit 813 can be placed. While the drainage container 814b is placed in the drainage container placement portion 814a in the present embodiment, the drainage container 814b is an optional, and may or may not be included. In the present embodiment, the drainage container 814b is a box having an upper opening, a wall on the storage container placement portion 815a side, extending upward, and a wall (upper surface) substantially parallel to the bottom surface of the observation target object treatment chamber, including the tip member detachment unit 814c formed as a semicircular recess (notch) at the upper end thereof. The drainage container 814b can collect a tip member detached from the suction/discharge unit 813. Thus, for example, the drainage container 814b can also be referred to as a tip member collection container, and the drainage container placement portion 814a can also be referred to as a tip member collection container placement portion. While the tip member detachment unit 814c is formed in the drainage container 814b, these members may be placed separately. The tip member detachment unit 814c may be placed in the vicinity of the suction/discharge unit 813, specifically in the arm 62 of the first moving unit 6 in which the suction/discharge unit 813 is placed.

The storage container placement portion 815a is a region in which the storage container 815b storing the tip member detachable from the suction/discharge unit 813 can be placed. While the storage container 815b is placed in the storage container placement portion 815a in the present embodiment, the storage container 815b is optional, and may or may not be included. The tip member is not particularly limited, and may be any member as long as it can store the liquid sucked by the suction/discharge unit 813 therein. For example, when the suction/discharge unit 813 is a pipettor, a tip member may be a chip. The storage container 815b may be, for example, a rack in which the chip is stored. The cell treatment apparatus 200 according to the present embodiment includes the tip member detachment unit 814c and the storage container placement portion 815a, and thus the movement of the members at the time of sucking and discharging the medium, the cells, and the like in the cell culture vessel 41 can be simplified (shortened).

The collection container placement portion 816a is a region where a collection container 816b for collecting a suction liquid containing the cells collected by the suction/discharge unit 813 can be placed. While the collection container 816b is placed in the collection container placement portion 816a in the present embodiment, the collection container 816b is optional, and may or may not be included. Examples of the collection container 816b include culture vessels such as known dishes and known flasks.

In the present embodiment, on the bottom surface of the observation target object treatment chamber, the drainage container placement portion 814a, the storage container placement portion 815a, the cell culture vessel placement unit 4, and the collection container placement portion 816a are disposed in this order on the plane on which the cell culture vessel placement unit 4 is placed, i.e., the XY plane along the moving direction of the XY stage 61 in the long axis direction (X-axis direction). However, these placement portions may not be placed along the long axis direction, and may not be placed in this order. In the present embodiment, the drainage container placement portion 814a, the storage container placement portion 815a, the cell culture vessel placement unit 4, and the collection container placement portion 816a are placed in the above-mentioned order. Thus, for example, the suction/discharge unit 813 can move linearly, and the movement of the members at the time of sucking and discharging the medium, the cells, and the like in the cell culture vessel 41 can be simplified (shortened).

As shown in FIG. 11, a camera 817, illumination lamps 818a and 818b, and a germicidal lamp 819 are provided above the opening 811a in the front wall of the observation target object treatment chamber in the cell treatment apparatus 200 according to the present embodiment. The illumination lamps 818a and 818b are placed on both sides of the camera 817 in the X-axis direction, and the germicidal lamp 819 is placed above the camera 817.

While the camera 817 is provided as the image sensor of the first chamber 81 in the present embodiment, the image sensor of the first chamber 81 is optional, and may or may not be included. The image sensor of the first chamber 81 is not limited to a camera and is only required to be able to image the inside of the first chamber 81, i.e., the observation target object treatment chamber. The image sensor of the first chamber 81 is not particularly limited, and a known image sensor such as a microscope or a camera can be used, and a combination of the known image sensor and a solid state image sensor (image sensor) such as a CCD or a Complementary MOS (CMOS) can be used. While the camera 817 is placed in the front wall of the observation target object treatment chamber, the position of the camera 817 is not particularly limited, and the camera 817 may be placed at any position and preferably placed to allow imaging a wide range in the observation target object treatment chamber. Specifically, in the case where the XY stage 61 and the arm 62, which are collectively the first moving unit 6, and the suction/discharge unit 813 are placed in back (the upper left side in FIG. 10) of the cell culture vessel placement unit 4 in the observation target object treatment chamber as in the cell treatment apparatus 200 according to the present embodiment, it is preferable to place the camera 817 in front (the lower right side in FIG. 10) of the observation target object treatment chamber so that an image of a wide range in the observation target object treatment chamber can be taken. It is preferable that the first image sensor can take an image at multiple magnifications (for example, different magnifications). However, the first image sensor may be able to take an image at one magnification. The magnification means, for example, an imaging magnification. As a specific example, the camera 817 includes lenses with multiple magnifications (for example, different magnifications). The image sensor of the first chamber 81 may be able to perform optical zooming, digital zooming, or the like, for example. The cell treatment apparatus 200 according to the present embodiment includes a camera 817. Thus, for example, the operation inside the observation target object treatment chamber can be checked, and the reliability of the operation can be improved. The number of the image sensors of the first chamber 81 placed inside the observation target object treatment chamber is not particularly limited, and may be one or more.

While the illumination lamps 818a and 818b are provided as the illumination unit in the present embodiment, the illumination unit is optional, and may or may not be included. The illumination unit is not limited to the illumination lamp and is only required to be able to project light (illuminate) inside the observation target object treatment chamber. The illumination unit is not particularly limited, and, for example, a known illumination such as a fluorescent lamp or a LED lamp can be used. While the illumination lamps 818a and 818b are placed in the front wall inside the observation target object treatment chamber in the present embodiment, the positions of the illumination lamps 818a and 818b are not particularly limited and the illumination lamps 818a and 818b can be placed at any positions. Preferably, the illumination lamps 818a and 818b are placed such that they can project light onto a wide range in the observation target object treatment chamber, i.e., they less prone to throw shades in the observation target object treatment chamber. Specifically, in the case where the XY stage 61 and the arm 62, which are collectively the first moving unit 6, and the suction/discharge unit 813 are placed in back (the upper left side in FIG. 10) of the cell culture vessel placement unit 4 in the observation target object treatment chamber as in the cell treatment apparatus 200 according to the present embodiment, it is preferable to place the illumination lamps 818a and 818b in front (the lower right side in FIG. 10) of the observation target object treatment chamber so that light can be projected onto a wide range in the observation target object treatment chamber. The cell treatment apparatus 200 according to the present embodiment includes the illumination lamps 818a and 818b. Thus, for example, the operation inside the observation target object treatment chamber can be checked, and the reliability of the operation can be improved. The number of the illumination units placed inside the observation target object treatment chamber is not particularly limited, and may be one or more.

While a germicidal lamp 819 is provided as a germicidal unit in the present embodiment, the germicidal unit is optional, and may or may not be included. Moreover, the germicidal unit is not limited to the germicidal lamp and is only required to be able to disinfect the inside of the observation target object treatment chamber, specifically, the periphery of the cell culture vessel placement unit 4. The germicidal unit is not particularly limited, and for example, a known germicidal unit such as a germicidal lamp, an ultraviolet LED lamp, or the like can be used. While the germicidal lamp 819 is placed in the front wall inside the observation target object treatment chamber in the present embodiment, the position of the germicidal lamp 819 is not particularly limited, and the germicidal lamp 819 may be placed at any position. For example, dust and the like outside the cell treatment apparatus 200 enter through the openings 811a and 811b. It is thus preferable that the germicidal lamp 819 is placed so as to be able to disinfect the vicinities of the openings 811a and 811b. Specifically, in the case where the opening 811a is provided in the front wall of the observation target object treatment chamber as in the cell treatment apparatus 200 according to the present embodiment, the germicidal unit is preferably placed above the opening 811a in the front wall of the observation target object treatment chamber. In the case where the opening 811b is provided in the wall on the side surface side of the observation target object treatment chamber as in the cell treatment apparatus 200 according to the present embodiment, the germicidal unit is preferably placed above the opening 811b in the wall on the side surface side of the observation target object treatment chamber. When the cell treatment apparatus 200 includes the illumination unit and the germicidal unit, both of them are preferably placed on the same wall of the observation target object treatment chamber, for example, on a wall in which the opening 811a is provided. In this case, the germicidal unit is provided preferably above the illumination unit. The cell treatment apparatus 200 according to the present embodiment includes a germicidal lamp 819. Thus, for example, the cleanliness of the interior of the observation target object treatment chamber is improved. The number of germicidal units placed in the observation target object treatment chamber is not particularly limited, and may be one or more.

In the present embodiment, as to the size, shape, structure, and the like of the observation target object treatment chamber, which is the first chamber 81, reference can be made to those of the safety cabinet, for example, and as a specific example, reference can be made to the safety cabinet standard specified in EN12469:2000.

As shown in FIGS. 12A and 12B, the cell culture vessel placement unit 4 in the cell treatment apparatus 200 according to the present embodiment includes an upper lid 43 and a bottom 44, and the upper lid 43 is detachably attached to the bottom 44. In the present embodiment, the cell culture vessel placement unit 4 is a box having the upper lid 43 and the bottom 44, and cell culture vessel 41 is placed inside the box. However, the cell culture vessel placement unit 4 is not limited thereto as long as the following is satisfied: the cell culture vessels 41 can be placed in the cell culture vessel placement unit 4, the cell culture vessel placement unit 4 is placed so as to be adjacent to the second chamber 82 in the observation target object treatment chamber, and the adjacent portion (bottom plate 47 in FIGS. 12A and 12B) of the cell culture vessel placement unit 4 to the second chamber 82 is translucent. The "translucent" means, for example, that the laser emitted from the laser irradiation unit 85 of the second chamber 82 can be transmitted. Also, the "translucent" means that the image sensor 34 of the observation unit can perform imaging through the bottom plate 47. A translucent region 45 is provided in the upper lid 43 so that the cell culture vessel 41 can be irradiated with light from the light source 1. The translucent region 45 is formed of, for example, a transparent glass plate, an acrylic plate, or the like. The bottom 44 includes a bottom wall 46 and a translucent bottom plate 47. The translucent bottom plate 47 is formed of, for example, a transparent glass plate, an acrylic plate, or the like. The bottom plate 47 is adjacent to the second chamber 82. For this reason, it can also be said that the adjacent portion of the cell culture vessel placement unit 4 to the second chamber 82, i.e., the bottom plate 47 forms a part of the wall of the observation target object treatment chamber. The contact portion between the bottom plate 47 and the wall of the observation target object treatment chamber is preferably sealed by a sealing compound such as a packing, a sealing member, or the like, for example. As a result, for example, the gas in the second chamber 82 and dust contained in the gas can be prevented from flowing into the cell culture vessel placement unit 4 and the observation target object treatment chamber. The bottom wall 46 includes four recesses 48 in which four cell culture vessels 41 can be respectively placed, and the side surface of each recess 48 has a reversely tapered shape that narrows from the inside of the observation target object treatment chamber toward the outside of the observation target object treatment chamber (from top toward bottom in FIG. 12B). Each recess 48 includes a projection 49 projecting toward the inside of the recess 48 on the end side of the bottom plate 47. The bottom end of the cell culture vessel 41 is in contact with the projection 49. While the bottom wall 46 has four recesses 48 in the cell treatment apparatus 200 according to the present embodiment, the number of the recesses 48 in the bottom wall 46 is not limited thereto, and can be appropriately determined according to the number of the cell culture vessels 41 to be placed. The size of each recess 48 can be appropriately determined depending on the size of the cell culture vessel 41 to be placed. In the cell culture vessel placement unit 4 according to the present embodiment, the recess 48 has the above-described structure. Thus, for example, the cell culture vessel 41 can be placed in the cell culture vessel placement unit 4 regardless of the shape of the side surface of the cell culture vessel 41. In the cell treatment apparatus 200 according to the present embodiment, the bottom wall 46 is integrally formed with the wall of the bottom surface and the wall of the side surface. However, the bottom wall 46 is not limited thereto, and the wall of the bottom surface and the wall of the side surface may be different members. When the wall of the bottom surface and the wall of the side surface in the bottom wall 46 are configured by different members, for example, a plurality of bottom surface members for the bottom wall 46, having different numbers and sizes of recesses 48 can be provided in advance. Thus, for example, the bottom surface member for the bottom wall 46 can be replaced with a member having a suitable number of recesses with suitable sizes for placement of the cell culture vessels 41 depending on the size and number of the cell culture vessels 41.

As shown in FIGS. 13 and 14, in the cell treatment apparatus 200 according to the present embodiment, the circulator 84 includes an intake portion 84a, a circulation path 84b, a gas supply portion 84c, and a discharge portion 84d. Thereby, the circulator 84 circulates the gas in the observation target object treatment chamber.

The intake portion 84a intakes the gas in the observation target object treatment chamber. The intake portion 84a may intake gas outside the cell treatment apparatus 200 instead of or in addition to the gas in the observation target object treatment chamber. In the present embodiment, the intake portion 84a is placed in the vicinity of (e.g., directly below) the opening 811a of the observation target object treatment chamber. Specifically, the intake portion 84a has a plurality of openings (e.g., slits) formed on its upper surface (not shown) and is placed below the opening 811a such that the opening communicates with the opening 811a. By placing the intake portion 84a in the vicinity of the opening 811a of the observation target object treatment chamber as described above, for example, the gas outside the cell treatment apparatus 200 and the dust and the like contained in the gas can be prevented from flowing into the observation target object treatment chamber at the time when the operator opens the door 812a and works in the observation target object treatment chamber. The intake portion 84a may be placed in the vicinity of the opening 811b instead of or in addition to the opening 811a. The intake portion 84a may intake the gas in the observation target object treatment chamber by a blowing unit as a fan, for example.

The circulation path 84b connects the intake portion 84a with the gas supply portion 84c and the discharge portion 84d. In the present embodiment, the circulation path 84b is placed in a space between the outer wall and the inner wall and above the first chamber 81. The circulation path 84b is, for example, a hollow tube. One end of the circulation path 84b communicates with the intake portion 84a, and the other end communicates with the gas supply portion 84c and the discharge portion 84d. When the circulation path 84b is placed in a space between the outer wall and the inner wall as in the cell treatment apparatus 200 according to the present embodiment, for example, the size of the cell treatment apparatus 200 can be reduced. While the circulator 84 includes the circulation path 84b in the present embodiment, the circulation path 84b may or may not be included. In the latter case, the intake portion 84a is connected directly to, for example, the gas supply portion 84c and the discharge portion 84d. The circulation path 84b may blow the gas taken in by the intake portion 84a to the gas supply portion 84c and the discharge portion 84d by a blowing unit such as a fan, for example.

When the circulation path 84b includes the blowing unit, the blowing unit may be placed in the vicinity of the intake portion 84a, the gas supply portion 84c, or the discharge portion 84d, or may be placed in any of other positions such as the center of each of these members. It is preferable to place the blowing unit in the vicinity of the intake portion 84a because, the intake from the intake portion 84a is improved, and the dust and the like can be effectively prevented from flowing into the observation target object treatment chamber, for example, as compared to the downflow generated by the gas supply portion 84c to be described below. When the blowing unit is placed in the vicinity of the intake portion 84a, it is preferable that the blowing unit be placed in, for example, the second chamber 82 or the third chamber 83. As a specific example, when the circulation path 84b further includes the blowing unit in the cell treatment apparatus 200 according to the present embodiment, the blowing unit is placed in front (the lower left side in FIG. 8), that is, on the lower side of the intake portion 84a in the second chamber 82 or the third chamber 83. In this case, the circulation path 84b connects the intake portion 84a with the intake side of the blowing unit and connects the blowing side of the blowing unit with the gas supply portion 84c and the discharge portion 84d. That is, the circulation path 84b is placed in the second chamber 82 or the second chamber 82 and the third chamber 83, the space between the outer wall and the inner wall, and above the first chamber 81.

The gas supply portion 84c supplies a part of the gas taken in by the intake portion 84a into the observation target object treatment chamber. In the present embodiment, the gas supply portion 84c communicates with the upper end of the first chamber 81 such that the gas taken in by the intake portion 84a can be supplied into the observation target object treatment chamber. The gas supply portion 84c may supply the gas into the observation target object treatment chamber by the blowing unit such as a fan, for example. The gas supply portion 84c may include, for example, a gas purification unit. In this case, the gas supplied from the gas supply portion 84c into the observation target object treatment chamber passes through the gas purification unit. When the gas supply portion 84c includes the gas purification unit, for example, the dust or the like can be prevented from flowing into the observation target object treatment chamber. Examples of the gas purification unit include filters for collecting fine particulates such as a high efficiency particulate air filter (HEPA filter), an ultra-low penetration air filter (ULPA filter), and the like. In the cell treatment apparatus 200 according to the present embodiment, the upper part of the observation target object treatment chamber is connected to the gas supply portion 84c. Thus, for example, blowing air from the gas supply portion 84c causes downflow, which can more effectively prevent dust and the like from flowing into the observation target object treatment chamber from the opening 811a.

The discharge portion 84d discharges the remainder of the gas taken in by the intake portion 84a to the outside of the observation target object treatment chamber, specifically, to the outside of the cell treatment apparatus 200. In the present embodiment, the discharge portion 84d is placed at an upper end (topmost portion) of the cell treatment apparatus 200 such that the gas taken in by the intake portion 84a can be discharged to the outside of the cell treatment apparatus 200. When the discharge portion 84d is provided in the topmost portion of the cell treatment apparatus 200 in this manner, for example, the size of the cell treatment apparatus 200 can be reduced, and the dust stirred up due to discharge can be prevented from flowing into the observation target object treatment chamber. The discharge portion 84d may discharge the gas to the outside of the cell treatment apparatus 200 with a blowing unit such as a fan, for example. The discharge portion 84d may include, for example, the gas purification unit. In this case, the gas discharged from the discharge portion 84d to the outside of the cell treatment apparatus 200 passes through the gas purification unit. When the discharge portion 84d includes the gas purification unit, for example, fine particles or the like generated in the observation target object treatment chamber can be prevented from blowing out of the cell treatment apparatus 200.

In the circulator 84, as to the size, shape, structure, and the like of each portion, reference can be made to those of the safety cabinet, for example, and as a specific example, reference can be made to the safety cabinet standard specified in EN12469:2000.

As shown in FIG. 15A, in the cell treatment apparatus 200 according to the present embodiment, the second chamber 82 includes the second moving unit 7, the housing 87 accommodating the imaging optical system 3, and the laser irradiation unit 85. While the cell treatment apparatus 200 according to the present embodiment includes the second moving unit 7, the second moving unit 7 is optional as described above and the cell treatment apparatus 200 may or may not include either one of the second moving unit 7. The second moving unit 7 includes an XY stage 71 and carriages 711a and 711b. The XY stage 71 is placed on the plane on which the cell culture vessel placement unit 4 is placed, i.e., on the bottom surface of the second chamber 82 substantially parallel to the XY plane. On a common rail (moving path) in the Y-axis direction in the XY stage 71, two rails in the X-axis direction are placed so as to be movable on the common rail. The carriages 711a and 711b are placed on the two rails, respectively, in the X-axis direction so as to be movable on the respective rails. The laser irradiation unit 85 includes the laser light source 85a, the optical fiber 85b, and the laser emission portion 85c. Above the XY stage 71, the housing 87 accommodating the imaging optical system 3 is placed on the carriage 711b such that an objective lens 31 of the imaging optical system 3 faces upward (Z-axis direction) and that the laser emission port of the laser emission portion 85c of the laser irradiation unit 85 faces upward (Z-axis direction) on the carriage 711a. The carriage 711a is movable up and down in the vertical direction (Z-axis direction). The laser light source 85a is placed on the bottom surface of the second chamber 82 in a region which does not overlap with the movable range of the XY stage 71 in the second chamber 82. One end of the optical fiber 85b is optically connected to the laser light source 85a, and the other end thereof is optically connected to the laser emission portion 85c.

While the imaging optical system 3 and the laser irradiation unit 85 are movable by the XY stage 71, which is the second moving unit 7, in the cell treatment apparatus 200 according to the present embodiment, the laser irradiation unit 85 may be moved by a drive unit other than the second moving unit 7. In this case, the moving direction of the drive unit that can move the laser irradiation unit 85 is not particularly limited, and is, for example, any one direction, two directions, or all directions of the X-axis direction, the Y-axis direction, and the Z-axis direction. While the drive unit (laser moving unit) that can move the laser irradiation unit 85 and the second moving unit 7 share a rail in the Y-axis direction (first direction) in the present embodiment, the laser moving unit and the second moving unit 7 may be independent. As a specific example, as shown in FIG. 15B, the laser moving unit on the bottom surface of the second chamber 82 may be placed as an XY stage 71a, and the second moving unit 7 may be placed as an XY stage 71b, for example. The moving directions of the laser moving unit and the second moving unit 7 are not particularly limited, and are, for example, any one direction, two directions, or all directions of the X-axis direction, the Y-axis direction, and the Z-axis direction. When the laser moving unit can move the laser irradiation unit 85, for example, substantially orthogonal to the plane on which the cell culture vessel placement unit 4 is placed, i.e., the bottom surface of the cell culture vessel 41, the laser moving unit can adjust a spot diameter to be described below. In this case, the laser moving unit also serves as, for example, a spot diameter adjusting unit to be described below. In the present embodiment, the XY stage 71 is a known stage that can move a target object at high speed and accurately along the X-axis direction and the Y-axis direction through a linear carriage cart or the like, for example.

It is preferable that the laser moving unit and the second moving unit 7 can move the laser irradiation unit 85 and the second imaging device in the first direction (for example, direction indicated by the arrow Y in FIG. 15A) in a plane substantially parallel to the plane on which the cell culture vessel placement unit 4 is placed as in the XY stage 71 of the present embodiment, respectively, and that the movement of the laser irradiation unit 85 in the first direction by the laser moving unit and the movement of the imaging optical system 3 in the first direction by the second moving unit 7 be on the same straight line. As described above, by moving the laser irradiation unit 85 and the imaging optical system 3 on the same straight line, for example, when performing cell treatment such as treating the cells in the cell culture vessel 41 by the laser irradiation unit 85 after being imaged by the imaging optical system 3, the number of times of moving each unit can be reduced, and the treatment time can be reduced.

Further, as in the XY stage 71 of the present embodiment, it is preferable that the laser moving unit include a carriage 711a on which the laser irradiation unit 85 is placed and a moving path (rail) placed along the first direction and along which the carriage 711a moves, and that the second moving unit 7 includes a carriage 711b on which the imaging optical system 3 is placed and a moving path (rail) placed along the first direction and along which the carriage 711b moves, wherein the moving path of the laser moving unit and the moving path of the imaging optical system 3 are the same. Such a configuration allows a reduction in the number of times of moving each unit when performing cell treatment such as treating the cells by the laser irradiation unit 85 after being imaged by the imaging optical system 3, and further reduce the treatment time. The second moving unit 7 is preferably configured to be movable independently of the first moving unit 6, as in the cell treatment apparatus 200 according to the present embodiment.

While the housing 87 that accommodates the imaging optical system 3 including the objective lens 31 having one magnification is placed as the imaging optical system 3 in the cell treatment apparatus 200 according to the present embodiment, the present invention is not limited thereto, and the housing 87 that accommodates the imaging optical system 3 including a plurality of types of objective lenses 31 may be placed. In this case, it is preferable that the magnifications of the plurality of types of objective lenses 31 be different magnifications such as, for example, 2×, 4×, and 8× respectively. In the case of including the imaging optical system 3 that includes the imaging device of the first chamber 81 and the objective lens 31 as in the cell treatment apparatus 200 according to the present embodiment, it is preferable that the magnification of the objective lens 31 of the imaging optical system 3 be higher than the magnification of the imaging device of the first chamber 81 so that the cells in the cell culture vessel 41 can be imaged more clearly.

While the laser irradiation unit 85 includes the laser light source 85a, the laser emission portion 85c, and the optical fiber 85b in the cell treatment apparatus 200 according to the present embodiment, the laser irradiation unit 85 is not limited thereto and is only required to be able to irradiate the cell culture vessel 41 placed in the cell culture vessel placement unit 4 with lasers. The laser irradiation unit 85 may include, for example, the laser light source 85a, and the cell culture vessel 41 may be irradiated with lasers directly from the laser light source 85a. Also, when the laser of the laser light source 85a is guided to the laser emission portion 85c, a light guiding unit such as a mirror, Micro Electro Mechanical Systems (MEMS), or the like may be used instead of the optical fiber 85b. However, the optical fiber 85b is preferable because the laser light source 85a can be freely placed in the second chamber 82, and, for example, by placing the laser light source 85a in a region in the second chamber 82 where other units such as the laser moving unit, the imaging optical system 3, and the second moving unit 7 are not placed and not overlapping with the movable range of other units, the size of the cell treatment device 200 can be reduced and the weight of the cell treatment apparatus 200 can be reduced compared to the case of using other light guiding unit.

The laser light source 85a is, for example, a device that oscillates a continuous wave laser or a pulsed laser. The laser light source 85a may be, for example, a high-frequency laser having a long pulse width close to a continuous wave. The output of the laser oscillated from the laser light source 85a is not particularly limited, and can be appropriately determined depending on, for example, treatment and cells. The wavelength of the laser oscillated by the laser light source 85a is not particularly limited, and can be, for example, a visible light laser, an infrared laser, or the like having a wavelength of 405 nm, 450 nm, 520 nm, 532 nm, 808 nm, or the like. As described above, when the laser absorbing layer is provided in the cell culture vessel 41, the laser light source 85a oscillates, for example, the laser having a wavelength that can be absorbed by the laser absorbing layer. Since the influence on the cells can be suppressed, it is preferable that the laser light source 85a oscillate a laser having a wavelength longer than 380 nm. As a specific example, the laser light source 85a can be a continuous wave diode laser having a wavelength in the vicinity of 405 nm and a maximum output of 5W.

When the laser irradiation unit 85 includes the laser emission portion 85c, it is preferable that the laser moving unit move the laser emission portion 85c. In addition, when the laser moving unit moves the laser emission portion 85c in the vertical direction (the direction indicated by the arrow Y in FIGS. 15A and 15B), it is preferable to move the laser emission portion 85c such that the laser emitting port of the laser emission portion 85c does not come into contact with the bottom surface of the observation target object treatment chamber, preferably, the bottom surface of the cell culture vessel placement unit 4. As a specific example, it is preferable that the laser moving unit move the laser emission portion 85c such that the laser emitting port of the laser emission portion 85c does not approach within 1 mm with reference to the bottom surface of the cell culture vessel placement unit 4. When the laser moving unit moves the laser emission portion 85c in such a range, for example, it is possible to prevent the sway pf the medium in the cell culture vessel 41 placed in the cell culture vessel placement unit 4, which caused by contact between the laser emission portion 85c and the bottom surface of the cell culture vessel placement unit 4.

In the present embodiment, the imaging optical system 3 is placed in front (on the lower left side in FIGS. 15A and 15B), and the laser irradiation unit 85 is placed in back (on the upper right side in FIGS. 15A and 15B). The positional relationship between the imaging optical system 3 and the laser irradiation unit 85, however, is not limited thereto, and for example, the imaging optical system 3 may be placed in back and the laser irradiation unit 85 may be placed in front. Generally, the volume of the imaging optical system 3 of the observation unit is larger than that of the laser irradiation unit 85. Thus, in the case where the cell culture vessel placement unit 4 is placed in front in the first chamber 81, the size of the cell treatment apparatus 200 can be reduced by placing the imaging optical system 3 in back and placing the laser irradiation unit 85 in front.

The cell treatment apparatus 200 according to the present embodiment may further include a spot diameter adjusting unit for adjusting the diameter of a spot formed on a site of an irradiation target object to be irradiated with lasers. The spot diameter means a beam diameter of a laser at a contact portion between the laser and the irradiation target object. The spot diameter can be adjusted, for example, by switching at least one of the laser condensing lens and the collimator lens (collimation lens) of the laser irradiation unit 85 or by changing the distance between the laser irradiation unit 85 and the irradiation target object. In the former case, preferably, the laser irradiation unit 85 includes, for example, a plurality of lenses, and the spot diameter adjusting unit adjusts the diameter of the spot by changing the lens. The plurality of lenses may be, for example, a plurality of condensing lenses, a plurality of collimator lenses, or a combination of one or more condensing lenses and one or more collimator lenses. The plurality of condensing lenses have different focal lengths, for example. The plurality of collimator lenses have different focal lengths, for example. The lens may be changed manually, for example, or may be changed by the control unit 5 described below. In the latter case, for example, the laser irradiation unit 85 includes a lens changing unit, and the lens is changed by the changing unit. When the spot diameter adjusting unit changes the distance, it is preferable that the spot diameter adjusting unit adjusts the diameter of the spot by adjusting the distance between the laser irradiation unit 85 and the irradiation target object. The distance between the laser irradiation unit 85 and the irradiation target object means, for example, a distance in a direction substantially orthogonal to the plane on which the cell culture vessel placement unit 4 is placed, i.e., the bottom surface of the cell culture vessel 41. When the laser irradiation unit 85 includes the laser emission portion 85c, the distance between the laser irradiation unit 85 and the irradiation target object means the distance between the laser emission portion 85c and the irradiation target object. The distance between the laser irradiation unit 85 and the irradiation target object can be adjusted by, for example, the laser moving unit. As a specific example, the distance between the laser irradiation unit 85 and the bottom surface of the cell culture vessel 41, which is the irradiation target object, can be adjusted by the movement by the laser moving unit in the direction of the arrow Z. In the cell treatment apparatus 200 according to the present embodiment, the carriage 711a of the XY stage 71 serving as the laser moving unit is movable up and down in the vertical direction (arrow Z direction). Thus, the laser moving unit in the present embodiment can be referred to as, for example, a spot diameter adjusting unit. In the case of performing cell treatment in which a small spot diameter is preferable, for example, in the case of performing division of a cell mass, excision of a cell or a cell mass from a specific region, or the like, the spot diameter adjusting unit adjusts the spot diameter to be small, for example. On the other hand, in the case of performing cell treatment in which a large spot diameter is preferable, for example, in the case of killing cell or the like in a specific region, the spot diameter adjusting unit adjusts the spot diameter to be large, for example. The size of the spot diameter is not particularly limited, and can be appropriately set depending on, for example, the type of cell treatment, the size of the cell, and the like. Since the cell treatment apparatus 200 according to the present embodiment includes the spot diameter adjusting unit, for example, the spot diameter can be adjusted to an appropriate size by the treatment performed on the cells, and the cell treatment can be performed quickly. In addition, since the spot diameter can be adjusted to an appropriate size, for example, the influence on cells not to be treated can be reduced.

When the cell treatment apparatus 200 according to the present embodiment includes the spot diameter adjusting unit, it is preferable that the control unit 5 described below control the adjustment of the diameter of the spot by the spot diameter adjusting unit.

In the cell treatment apparatus 200 according to the present embodiment, it is preferable that the gas is prevented from moving between the observation target object treatment chamber and the second chamber 82. The gas can be prevented from moving, for example, by sealing the adjacent portion of the observation target object treatment chamber to the second chamber 82 with a sealing compound such as a packing, a sealing member, or the like. By preventing the gas from moving in this manner, for example, the dust contained in the gas can be prevented from flowing into the observation target object treatment chamber.

In the cell treatment apparatus 200 according to the present embodiment, the third chamber 83 includes the control unit 5 and the power supply unit 57. As shown in FIG. 16, in the control unit 5 of the present embodiment, the I/O interface 55 is a device that can communicate with and control the members such as the DMD 22, the first moving unit 6, the second moving unit 7, the suction/discharge unit 813, the camera 817, the observing unit, the laser irradiation unit 85, and the like. Except for this point, the control unit 5 of the present embodiment has the same configuration as the control unit 5 of the first embodiment, and reference can be made to the description thereof.

In the cell treatment apparatus 200 according to the present embodiment, the control unit 5 has the functions of controlling the DMD 22, the first moving unit 6, the second moving unit 7, the suction/discharge unit 813, the camera 817, the observing unit, and the laser irradiating unit 85, so that a control unit does not have to be individually provided in each member, whereby the size of the device can be reduced. The present invention, however, is not limited thereto. In the cell treatment apparatus of the present embodiment, for example, a control unit as the control unit 5 may be provided in each of the DMD 22, the first moving unit 6, the second moving unit 7, the suction/discharge unit 813, the camera 817, the observing unit, and the laser irradiation unit 85, and each member may be controlled by the control unit of each member. The cell treatment apparatus of the present invention may include, for example, the control unit 5 and the control units of the respective members to control the members in cooperation.

While the control unit 5 controls the observation unit and the laser irradiation unit 85 in the present embodiment, the control unit 5 may control either one of them.

While the control unit 5 controls the laser irradiation by the laser irradiation unit 85 and the movement of the laser emission portion 85c of the laser irradiation unit 85 by the XY stage 71 and the carriage 711a, which are collectively the laser moving unit, in the present embodiment, the control unit 5 may control either one of them.

While the control unit 5 controls the suction and discharge by the suction/discharge unit 813 and the movement of the suction/discharge unit 813 by the XY stage 61 and the arm 62, which are collectively the first moving unit 6 in the present embodiment, the control unit 5 may control either one of them.

In the present embodiment, the control unit 5 controls the imaging of the inside of the observation target object treatment chamber by the camera 817 which is the imaging device of the first chamber 81.

While the control unit 5 controls the ON/OFF of the light source 1, the movement of the illumination optical system 2 by the XY stage 61 and the arm 62, which are collectively the first moving unit 6, the imaging of the observation target object by the image sensor 34 of the imaging optical system 3, and the movement of the imaging optical system 3 by the XY stage 71 and the carriage 711*b*, which are collectively the second moving unit 7, in the present embodiment, the control unit 5 may control one or more of them.

The power supply unit 57 is not particularly limited, and a known power supply can be used. The power supply unit 57 supplies electric power to members (units) activated by electric power, such as the laser irradiation unit 85, the observation unit, the first moving unit 6, the second moving unit 7, the suction/discharge unit 813, the circulator 84, the illumination unit, the germicidal unit, the control unit 5, and the like. Thus, the power supply unit 57 is electrically connected to, for example, the members (units) activated by electric power. The power supply unit 57 supplies electric power at a voltage of, for example, 100 V. This enables the cell treatment apparatus 200 to be used even in a general electric power environment, for example. In the cell treatment apparatus 200 according to the present embodiment, the power supply unit 57 is responsible for the entire power supply, so that a power supply unit is not required to be provided individually for each member, whereby the size and weight of the cell treatment apparatus 200 can be reduced, for example. The present invention, however, is not limited thereto, and, for example, a dedicated power supply unit may be provided for at least one of the units.

The cell treatment apparatus 200 according to the present embodiment may further include a communication portion (not shown) in the third chamber 83. The communication portion has a function of transmitting/receiving data to/from an external device such as a personal computer, a mobile communication device, or the like, or a function of connecting to the Internet or the like, for example, by wire or wireless communication. The communication portion may be, for example, an existing communication module or the like. When a communication portion is provided as described above, the cell treatment apparatus 200 can be connected to the outside. Thus, the cell treatment apparatus 200 can be operated from the outside or can receive data from the outside, for example. In addition, data in the cell treatment apparatus 200 can be browsed by, for example, connecting from the outside.

Next, treatment of cells and collection of treated cells using the cell treatment apparatus 200 according to the present embodiment will be described with reference to examples.

First, the germicidal lamp 819 is turned off, and the illumination lamps 818*a* and 818*b* are turned on. In addition, the camera 817 is activated by the control unit 5 to start imaging inside of the observation target object treatment chamber. The image of the inside of the observation target object treatment chamber taken by the camera 817 is output to a display device via, for example, the control unit 5. Further, the circulator 84 is activated to circulate the gas in the observation target object treatment chamber. Thereafter, an operator opens the door 812*a* of the opening 811*a*, places the cell culture vessel 41 in the cell culture vessel placement unit 4, and places the collection container 816*b* in the collection container placement portion 816*a*. The laser absorbing layer is formed on the bottom surface of the cell culture vessel 41. After the placement, the operator closes the door 812*a* of the opening 811*a*.

Next, the control unit 5 controls the XY stage 71 and the carriage 711*b* to move, thereby moving the housing 87 accommodating the imaging optical system 3 to below the bottom surface of the cell culture vessel 41. Further, the control unit 5 controls the XY stage 61 to move, thereby moving the housing 86 accommodating the illumination optical system 2 to above the upper surface of the cell culture vessel 41, i.e., to above the cell culture vessel placement unit 4. Then, the tile images of the cell culture vessel 41 are acquired in the same manner as in the imaging method by the phase difference observation apparatus 100 of the first embodiment. The tile images may be acquired by using the objective lenses 31 having different magnifications depending on the size of the observation target object 42 to be treated, for example. The image taken by the image sensor 34 may be, for example, a phase difference image taken by a phase-contrast microscope. When the imaging optical system 3 can perform fluorescence observation, the image taken by the image sensor 34 may be a fluorescence image. The taken image is output to the display device via, for example, the control unit 5.

For example, when the operator designates a treatment target region (e.g., a region of cells to be collected) by the input device on the basis of the taken tile images, the control unit 5 controls the XY stage 71 and the carriage 711*a* to move, thereby moving laser emission port 85*c* to a position where target objects such as cells surrounding the treatment target region can be irradiated with lasers below the bottom surface of the cell culture vessel 41. The control unit 5 controls the laser light source 85*a* to oscillate a laser. The oscillated laser is guided by the optical fiber 85*b* and emitted from the laser emission port 85*c*. Further, with the laser irradiation, the XY stage 71 and the carriage 711*a* are moved around the treatment target region by the control unit 5. At this time, the size of the spot diameter is adjusted to an appropriate size by moving the carriage 711*a* up and down in accordance with the size of the cells surrounding the region of the cells to be treated so as not to affect the observation target objects 42 in the treatment target region. The irradiated laser is absorbed by the laser absorbing layer formed on the bottom surface of the cell culture vessel 41, and target objects surrounding the treatment target region are killed by heat or the like generated from the laser absorbing layer. This makes it possible to excise the treatment target region.

Next, the control unit 5 controls the XY stage 61 to move, thereby moving the suction/discharge unit 813 to above the storage container 815*b*. The control unit 5 controls the arm 62 to move up and down, thereby attaching a chip, which is the tip member, to the suction/discharge port side of the suction/discharge unit 813. Next, the control unit 5 controls the XY stage 61 to move, thereby moving the suction/discharge unit 813 to above the treatment target region in the cell culture vessel 41. The control unit 5 controls the arm 62 to move down, thereby placing the opening of the chip in the vicinity of the treatment target region. In this state, the control unit 5 controls the suction/discharge unit 813 to suck the observation target objects 42 in the treatment target region together with the surrounding medium into the chip.

Further, the control unit 5 controls the arm 62 to move up and the XY stage 61 to move, thereby moving the suction/discharge unit 813 to above the collection container 816*b*. Further, the control unit 5 controls the arm 62 to move down, thereby moving the opening of the chip to the inside of the collection container 816*b*. In this state, the control unit 5 controls the suction/discharge unit 813 to discharge the medium containing the observation target objects 42 in the treatment target region in the chip into the collection container 816b.

After the discharge, the control unit 5 controls the arm 62 to move up and the XY stage 61 to move, thereby moving the suction/discharge unit 813 to above the drainage container 814b. Further, the control unit 5 controls the arm 62 to move down and the XY stage 61 to move, thereby catching the upper end of the chip by the tip member detachment unit 814c, which is a recess in the upper surface provided on the drainage container 814b. In this state, the control unit 5 controls the arm 62 to move up, thereby detaching the chip from the suction/discharge unit 813.

Then, the operator opens the door 812a of the opening 811a, collects the cell culture vessel 41 from the cell culture vessel placement unit 4, and collects the collection container 816b from the collection container placement portion 816a. In this manner, the cell treatment apparatus 200 according to the present embodiment can treat observation target objects 42 such as cells and collect the treated observation target objects 42.

According to the cell treatment apparatus 200 of the present embodiment, the deterioration of the phase difference image due to the meniscus can be suppressed, so that the phase difference image having a large contrast can be taken by the observation unit. On the basis of the phase difference image having a large contrast, the observation target object 42, the region, and the like to be subjected to the laser treatment can be clarified, so that the laser treatment can be performed with high accuracy. Therefore, according to the cell treatment apparatus 200 of the present embodiment, for example, damage at the time of laser treatment can be reduced.

The cell treatment apparatus 200 according to the present embodiment can easily subject the cells in the cell culture vessel 41 to treatments such as selection and collection, for example. In addition, since the cell treatment apparatus 200 according to the present embodiment treats the cells not by the operator but by the laser irradiation unit 85, for example, the operation is not affected by the skill level of the operator. Thus, for example, the quality of the cells obtained after the treatment is stabilized.

EXAMPLES

Next, examples of the present invention will be described. The present invention, however, is not limited by the following examples. Commercially available reagents were used on the basis of the protocols thereof unless otherwise noted.

Example 1

The present example examined that the deterioration of the phase difference image due to the meniscus can be suppressed by imaging cells in the cell culture vessel using the phase difference observation apparatus of the present invention.

Figure 18:
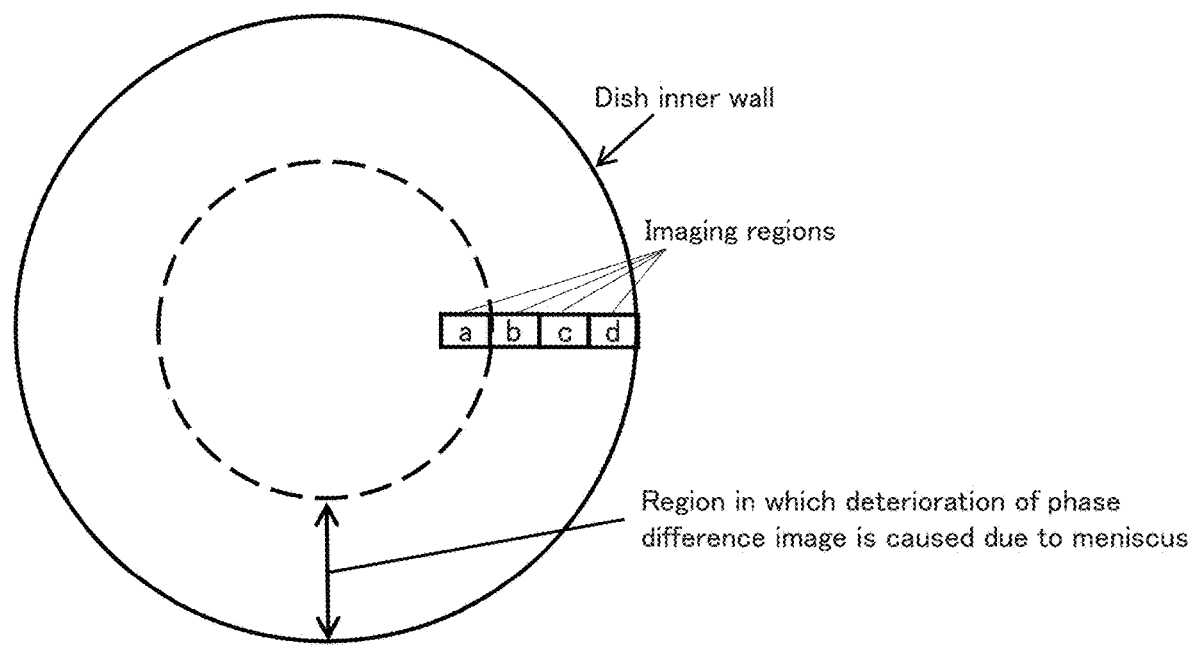
FIG. 18 is a schematic view showing the region in the cell culture vessel to be imaged using the phase difference observation apparatus of the present invention in Example 1.

When 3 mL of culture solution is introduced into a 35-mm (diameter) dish (IWAKI), the meniscus causes degradation of the phase difference image in the range about 7 mm from the wall surface (the region between the broken line and the solid line), as shown by the arrow in FIG. 18. In Example 1, the phase difference observation apparatus 100 was used to image the regions a to d shown in FIG. 18 of the dish into which the culture solution had been introduced. Specifically, the regions a to d were imaged by the imaging method shown in FIG. 7 after the intensity distribution correction information was acquired by the acquisition method shown in FIG. 6. Each step in the acquisition method shown in FIG. 6 was performed by the user. The intensity distribution of the next illumination light was set by moving the illumination image. Among the regions a to d, the regions b to d are regions in which deterioration of the phase difference image is caused due to the meniscus. Thus, the region b was corrected using intensity distribution correction information including the intensity distribution of one illumination light, thereby acquiring an image (corrected image 1). The region c was corrected using intensity distribution correction information including two intensity distributions of illumination light to acquire two images (corrected images 2 and 3), and then one image was acquired by integrating the correction target regions. The region d was corrected using intensity distribution correction information including three intensity distributions of illumination light to acquire three images (corrected images 4 to 6), and then one image was acquired by integrating the correction target regions. The results are shown in FIG. 19.

FIG. 19 is a photograph showing a phase difference image taken by the phase difference observation apparatus 100. As shown in FIG. 19, in the region a having no meniscus, the deterioration of the phase difference image was not observed even in the state of not being corrected. On the other hand, while the deterioration of the phase difference image was observed in the regions b to d having meniscus, by adopting or integrating the images (corrected images 2 to 6) obtained by the correction on the basis of the intensity distribution correction information, the deterioration of the phase difference image in these regions could be further suppressed.

These results showed that the deterioration of the phase difference image due to the meniscus could be suppressed by imaging cells in the cell culture vessel using the phase difference observation apparatus of the present invention.

Example 2

The present example examined that the phase difference observation apparatus of the present invention enlarges a region where an image can be taken while suppressing the deterioration of the phase difference image due to the meniscus.

The entire surface of the 35-mm dish into which 3 mL of culture solution had been introduced was imaged to produce a phase difference image in the same manner as in Example 1. As a control, the phase difference image was taken in the same manner except that the correction on the basis of the intensity distribution correction information and the correction value of the intensity distribution correction information were not used. Then, as to each phase difference image, the area of the region in which the meniscus is suppressed, i.e., the region in which the cells in the dish can be observed was calculated. In addition, as to the images before and after the correction by the correction value of the intensity distribution correction information, the mean value ($R_A$) of the distances from the wall surface of the 35-mm dish to the observable region was calculated.

Next, as to a 60-mm (diameter) dish (φ 60, IWAKI) and a 100-mm (diameter) dish (φ100, IWAKI), the area of an observable region in which the cells in the dish before and after the correction by the correction value of the intensity distribution correction information can be observed was calculated on the basis of the mean value ($R_A$) of the distances from the wall surface to the observable region in the 35-mm dish. The results are shown in Table 1 below.

TABLE 1

| Dish type | φ 35 | φ 60 | φ 100 |
|---|---|---|---|
| Culture area (mm²) | 900 | 2100 | 5500 |
| Observable area before correction (mm²) | 310 (34%) | 1120 (53%) | 3820 (69%) |
| Observable area after correction (mm²) | 800 (89%) | 1940 (92%) | 5420 (95%) |

As shown in Table 1, the phase difference observation apparatus 100 remarkably enlarged the observable region in the dish, and the effect was significant especially in the case of the dish having a small diameter.

These results showed that the phase difference observation apparatus of the present invention enlarged a region where an image can be taken while suppressing the deterioration of the phase difference image due to the meniscus.

The invention of the present application was described above with reference to the embodiments. However, the invention of the present application is not limited to the above-described embodiments. Various changes that can be understood by those skilled in the art can be made in the configurations and details of the invention of the present application within the scope of the invention of the present application.

This application claims priority from Japanese Patent Application No. 2017-189170 filed on Sep. 28, 2017 and Japanese Patent Application No. 2018-110020 filed on Jun. 8, 2018. The entire subject matter of the Japanese Patent Applications is incorporated herein by reference.

<Supplementary Notes>

A part of or the whole of the above-described embodiments and examples can be described as the following supplementary notes. However, the present invention is by no means limited thereto.

(Supplementary Note 1)

A phase difference observation apparatus, including:
a light source;
an illumination optical system that guides illumination light from the light source to an observation target object in a cell culture vessel;
an imaging optical system that forms an optical image of the observation target object on an image sensor; and
a control unit, wherein
the illumination optical system includes a spatial modulator that changes an intensity distribution of the illumination light,
the control unit contains intensity distribution correction information associating a position of the imaging optical system with respect to the cell culture vessel with an intensity distribution of illumination light at the position of the imaging optical system,
the control unit acquires imaging system position information, which is the position of the imaging optical system, and
the control unit changes an intensity distribution of illumination light in the spatial modulator on the basis of the imaging system position information and the intensity distribution correction information.

(Supplementary Note 2)

The phase difference observation apparatus according to Supplementary Note 1, wherein
the imaging optical system includes a phase plate, and
the intensity distribution of illumination light in the intensity distribution correction information is intensity distribution of illumination light with which an illumination image, which is an image of the illumination light, is included in a phase plate image, which is an image of the phase plate, at the position of the imaging optical system.

(Supplementary Note 3)

The phase difference observation apparatus according to Supplementary Note 1 or 2, wherein
the imaging optical system includes a phase plate,
the control unit obtains, as to a cell culture vessel containing no observation target object, an intensity distribution of illumination light with which an illumination image, which is an image of the illumination light, is included in a phase plate image, which is an image of the phase plate, at the position of the imaging optical system, and
the control unit stores the obtained intensity distribution of illumination light and the position of the imaging optical system in association with each other as the intensity distribution correction information.

(Supplementary Note 4)

The phase difference observation apparatus according to any one of Supplementary Notes 1 to 3, wherein
the spatial modulator includes a digital micromirror device that guides the illumination light by reflecting it toward the observation target object.

(Supplementary Note 5)

The phase difference observation apparatus according to any one of Supplementary Notes 1 to 4, including:
a first moving unit that can move the light source and the illumination optical system, wherein
the control unit controls movement by the first moving unit.

(Supplementary Note 6)

The phase difference observation apparatus according to Supplementary Note 5, wherein
the imaging optical system includes a phase plate, and
the first moving unit is movable in a direction perpendicular to a plane of the phase plate.

(Supplementary Note 7)

The phase difference observation apparatus according to any one of Supplementary Notes 1 to 6, wherein
the control unit stores illumination system position correction information associating the position of the imaging optical system with positions of the light source and the illumination optical system, and
the control unit corrects the positions of the light source and the illumination optical system on the basis of the imaging system position information and the illumination system position correction information.

(Supplementary Note 8)

The phase difference observation apparatus according to any one of Supplementary Notes 1 to 7, wherein
the control unit divides an imaging target region of the cell culture vessel into a plurality of sections,
the control unit changes the intensity distribution of illumination light in the spatial modulator on the basis of the imaging system position information and the intensity distribution correction information, and images each section by the image sensor, and
the control unit produces an image of the imaging target region of the cell culture vessel on the basis of the obtained images.

(Supplementary Note 9)

The phase difference observation apparatus according to Supplementary Note 8, wherein
the control unit determines whether there is an imaging defective site in the image of the imaging target region, the control unit calculates a correction value of the intensity distribution correction information of a section containing the imaging defective site if there is one, the control unit re-images the section containing the imaging defective site by the image sensor on the basis of the imaging system position information, the intensity distribution correction information, and the correction value of the intensity distribution correction information, and the control unit changes an image of the section containing the imaging defective site with the image obtained by the re-imaging to produce the image of the imaging target region.

(Supplementary Note 10)

The phase difference observation apparatus according to any one of Supplementary Notes 1 to 9, wherein the control unit obtains, as to the cell culture vessel containing no observation target object, the intensity distribution of illumination light with which an illumination image, which is an image of the illumination light, is included in a phase plate image, which is an image of the phase plate, at the position of the imaging optical system, the control unit changes the intensity distribution of illumination light in the spatial modulator with the obtained intensity distribution of illumination light, images by the image sensor, and determines whether a luminance value in a pixel of the obtained image is equal to or more than a reference luminance value, if the luminance value in the image is equal to or more than the reference luminance value, the control unit changes, as to a region in which the luminance value in the image is equal to or more than the reference luminance value, the illumination image, which is the image of the illumination light, at the position of the imaging optical system, and obtain an intensity distribution of a next illumination light, and the control unit stores each obtained intensity distribution of illumination light and the position of the imaging optical system in association with each other as the intensity distribution correction information.

(Supplementary Note 11)

The phase difference observation apparatus according to Supplementary Note 10, wherein the control unit determines whether the intensity distribution correction information associated with the imaging system position information includes a plurality of intensity distributions of illumination light, if the intensity distribution correction information includes a plurality of intensity distributions of illumination light, the control unit changes the intensity distribution of illumination light in the spatial modulator with the plurality of intensity distributions of illumination light, and images by the image sensor, and in each of the obtained images, the control unit extracts a region in which the luminance value in the pixel of the obtained image is less than the reference luminance value, and integrates the extracted images.

(Supplementary Note 12)

The phase difference observation apparatus according to any one of Supplementary Notes 1 to 11, including:

a cell culture vessel placement unit in which the cell culture vessel can be placed, wherein the cell culture vessel placement unit is placed between the illumination optical system and the imaging optical system in an optical path of the illumination light.

(Supplementary Note 13)

The phase difference observation apparatus according to Supplementary Note 12, wherein a position of the cell culture vessel placement unit in the phase difference observation apparatus is fixed.

(Supplementary Note 14)

The phase difference observation apparatus according to any one of Supplementary Notes 1 to 13, including:

a second moving unit that can move the imaging optical system, wherein the control unit controls the movement of the second moving unit.

(Supplementary Note 15)

The phase difference observation apparatus according to any one of Supplementary Notes 1 to 14, wherein the spatial modulator is placed at a position optically conjugate to a pupil of the imaging optical system.

(Supplementary Note 16)

A cell treatment apparatus including:

an observation unit that can observe an observation target object in a cell culture vessel;

a laser irradiation unit that can irradiate the observation target object with lasers; and a control unit that controls at least one of the observation unit or the laser irradiation unit, wherein the observation unit is the phase difference observation apparatus according to any one of Supplementary Notes 1 to 15.

(Supplementary Note 17)

The cell treatment apparatus according to Supplementary Note 16, including:

a first region;

a second region; and a third region, wherein the first region and the second region are placed contiguously, the first region is an observation target object treatment chamber for treating the observation target object in the cell culture vessel, the observation target object treatment chamber includes a cell culture vessel placement unit in which the cell culture vessel can be placed, the first region includes a light source and an illumination optical system in the observation unit, the second region includes an imaging optical system in the observation unit and the laser irradiation unit, the third region includes the control unit, and the cell culture vessel placement unit is placed adjacent to the second region in the observation target object treatment chamber.

INDUSTRIAL APPLICABILITY

According to the phase difference observation apparatus of the present invention, for example, since an additional imaging unit is not required, the size of the apparatus can be reduced, and deterioration of the phase difference image due to the meniscus can be suppressed. Therefore, the present invention is considerably useful in, for example, the life science field, the medical field, and the like in which observation target objects such as cells, tissues, and the like are observed.

REFERENCE SIGNS LIST

1: light source
2: illumination optical system
21: light source lens
22: digital micromirror device
23: condenser lens
3: imaging optical system
31: objective lens
32: phase plate
33: imaging lens
34: image sensor
35: phase plate imaging lens
4: cell culture vessel placement unit (stage)
41: cell culture vessel
42: observation target object
43: upper lid
44: bottom
45: translucent region
46: bottom wall
47: bottom plate
48: recess
49: projection
5: control unit
51: CPU
52: main memory
53: auxiliary storage device
54: video codec
55: I/O interface
56: controller
57: power supply unit
6: first moving unit
61, 71, 71a, 71b: XY stage
62: arm
7: second moving unit
711a, 711b: carriage
81: first room
811a, 811b: opening
812a, 812b: door
813: suction/discharge unit
814a: drainage container placement portion
814b: drainage container
814c: tip member detachment unit
815a: storage container placement portion
815b: storage container
816a: collection container placement portion
816b: collection container
817: camera
818a, 818b: illumination lamp
819: germicidal lamp
82: second room
83: third room
84: circulator
84a: intake portion
84b: circulation path
84c: gas supply portion
84d: discharge portion
85: laser irradiation unit
85a: laser light source
85b: optical fiber
85c: laser emission portion
86, 87: housing
100: phase difference observation apparatus
200: cell treatment apparatus

The invention claimed is:

1. A phase difference observation apparatus, comprising:
a light source;
an illumination guide that guides illumination light from the light source to an observation target object in a cell culture vessel;
an optical imager that forms an optical image of the observation target object on an image sensor; and
a central processing unit,
wherein the optical imager comprises:
a phase plate, and
an imaging lens,
wherein the illumination guide comprises:
a spatial modulator that changes an intensity distribution of the illumination light,
wherein the central processing unit:
stores intensity distribution correction information associating a position of the optical imager with respect to the cell culture vessel and an intensity distribution of the illumination light that is included in a phase plate image, formed upon a phase plate imaging lens being inserted between the imaging lens and the image sensor, at the position of the optical imager with respect to the cell culture vessel,
acquires position information of the optical imager, and
changes an intensity distribution of illumination light in the spatial modulator on a basis of the position information of the optical imager and the intensity distribution correction information to include an illumination light image in the phase plate image with an optical conjugation of the spatial modulator and the phase plate.

2. The phase difference observation apparatus according to claim 1, wherein an intensity distribution of illumination light in the intensity distribution correction information is intensity distribution of illumination light with which an illumination image, which is an image of the illumination light, is included in the phase plate image, which is an image of the phase plate, at the position of the optical imager.

3. The phase difference observation apparatus according to claim 1, wherein the central processing unit:
obtains, as to a cell culture vessel previously containing no observation target object, an intensity distribution of illumination light with which an illumination image, which is an image of the illumination light, is included in the phase plate image, which is an image of the phase plate, at the position of the optical imager, and
stores the obtained intensity distribution of illumination light and the position of the optical imager in association with each other as the intensity distribution correction information.

4. The phase difference observation apparatus according to claim 1, wherein
the spatial modulator comprises a digital micromirror device that guides the illumination light by reflecting it toward the observation target object.

5. The phase difference observation apparatus according to claim 1, comprising:
a first moving unit that can move the light source and the illumination guide,
wherein the central processing unit controls movement by the first moving unit.

6. The phase difference observation apparatus according to claim 5, wherein
the optical imager comprises the phase plate, and
the first moving unit is movable in a direction perpendicular to a plane of the phase plate.

7. The phase difference observation apparatus according to claim 1, wherein the central processing unit:
stores illumination system position correction information associating the position of the optical imager with positions of the light source and the illumination guide, and
corrects the positions of the light source and the illumination guide on the basis of the position information of the optical imager and the illumination system position correction information.

8. The phase difference observation apparatus according to claim 1, wherein the central processing unit:
divides an imaging target region of the cell culture vessel into a plurality of sections,
changes the intensity distribution of illumination light in the spatial modulator on the basis of the position information of the optical imager and the intensity distribution correction information, and images each section on the image sensor, and
produces an image of the imaging target region of the cell culture vessel on a basis of the obtained images.

9. The phase difference observation apparatus according to claim 8, wherein the central processing unit:
determines whether there is an imaging defective site in the image of the imaging target region,
calculates a correction value of the intensity distribution correction information of a section containing the imaging defective site, wherein an imaging defective site is in the image of the imaging target region,
re-images the section containing the imaging defective site by the image sensor on the basis of the position information of the optical imager, the intensity distribution correction information, and the correction value of the intensity distribution correction information, and
changes an image of the section containing the imaging defective site with the image obtained by the re-imaging to produce the image of the imaging target region.

10. The phase difference observation apparatus according to claim 1, wherein the central processing unit:
obtains, as to the cell culture vessel previously containing no observation target object, the intensity distribution of illumination light with which an illumination image, which is an image of the illumination light, is included in the phase plate image, which is an image of the phase plate, at the position of the optical imager,
changes the intensity distribution of illumination light in the spatial modulator with the obtained intensity distribution of illumination light, images by the image sensor, and determines whether a luminance value in a pixel of the obtained image is equal to or more than a reference luminance value,
changes, as to a region in which the luminance value in the image is equal to or greater than the reference luminance value, the illumination image, which is the image of the illumination light, at the position of the optical imager,
obtains an intensity distribution of a next illumination light,
wherein the luminance value in the image is equal to or greater than the reference luminance value, and
stores each obtained intensity distribution of illumination light and the position of the optical imager in association with each other as the intensity distribution correction information.

11. The phase difference observation apparatus according to claim 10, wherein the central processing unit:
determines whether the intensity distribution correction information associated with the position information of the optical imager includes a plurality of intensity distributions of illumination light,
changes the intensity distribution of illumination light in the spatial modulator with the plurality of intensity distributions of illumination light, and
images by the image sensor,
wherein the intensity distribution correction information includes a plurality of intensity distributions of illumination light, and
in each of the obtained images, the central processing unit extracts a region in which the luminance value in the pixel of the obtained image is less than the reference luminance value, and integrates the extracted images.

12. The phase difference observation apparatus according to claim 1, comprising:
a cell culture vessel placement unit in which the cell culture vessel can be placed, wherein
the cell culture vessel placement unit is placed between the illumination guide and the optical imager in an optical path of the illumination light.

13. The phase difference observation apparatus according to claim 12, wherein a position of the cell culture vessel placement unit in the phase difference observation apparatus is fixed.

14. The phase difference observation apparatus according to claim 1, comprising:
a second moving unit that can move the optical imager, wherein the central processing unit controls a movement of the second moving unit.

15. The phase difference observation apparatus according to claim 1, wherein the spatial modulator is placed at a position optically conjugate to a pupil of the optical imager.

16. A cell treatment apparatus comprising:
an observation unit that can observe the observation target object in a cell culture vessel;
a laser emitter that can irradiate the observation target object with lasers;
and wherein
the central processing unit controls at least one of the observation unit or the laser emitter, and
the observation unit is the phase difference observation apparatus according to claim 1.

17. The cell treatment apparatus according to claim 16, comprising:
a first region;
a second region; and
a third region, wherein
the first region and the second region are placed contiguously,
the first region is an observation target object treatment chamber for treating the observation target object in the cell culture vessel,
the observation target object treatment chamber comprises a cell culture vessel placement unit in which the cell culture vessel can be placed,
the first region comprises the light source and the illumination guide in the observation unit,
the second region comprises the optical imager in the observation unit and the laser emitter,
the third region comprises the central processing unit, and
the cell culture vessel placement unit is placed adjacent to the second region in the observation target object treatment chamber.

* * * * *